(12) United States Patent
Verkman et al.

(10) Patent No.: US 7,939,558 B2
(45) Date of Patent: May 10, 2011

(54) COMPOUNDS HAVING ACTIVITY IN INCREASING ION TRANSPORT BY MUTANT-CFTR AND USES THEREOF

(75) Inventors: Alan Verkman, San Francisco, CA (US); R. Kiplin Guy, Concord, CA (US); Nicoletta Pedemonte, San Francisco, CA (US); Luis J. V. Galietta, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 608 days.

(21) Appl. No.: 11/628,411

(22) PCT Filed: Jun. 2, 2005

(86) PCT No.: PCT/US2005/019346
§ 371 (c)(1),
(2), (4) Date: Jul. 9, 2008

(87) PCT Pub. No.: WO2005/120497
PCT Pub. Date: Dec. 22, 2005

(65) Prior Publication Data
US 2008/0319008 A1 Dec. 25, 2008

Related U.S. Application Data

(60) Provisional application No. 60/653,373, filed on Feb. 15, 2005, provisional application No. 60/576,966, filed on Jun. 4, 2004.

(51) Int. Cl.
*A61K 31/404* (2006.01)
*C07D 209/04* (2006.01)

(52) U.S. Cl. ........ 514/419; 548/469; 548/494; 548/495; 514/415

(58) Field of Classification Search .............. 548/469, 548/494, 495; 514/415, 419
See application file for complete search history.

(56) References Cited

U.S. PATENT DOCUMENTS

| 3,953,428 | A | 4/1976 | Murakami et al. | |
|---|---|---|---|---|
| 6,969,728 | B2 * | 11/2005 | Sneddon et al. | 514/400 |
| 7,034,031 | B2 * | 4/2006 | Sneddon et al. | 514/256 |
| 7,696,244 | B2 * | 4/2010 | Verkman et al. | 514/447 |

FOREIGN PATENT DOCUMENTS

| WO | WO0155106 | 8/2001 |
|---|---|---|
| WO | WO02074730 | 9/2002 |

OTHER PUBLICATIONS

Galietta, et al., Novel CFTR Chloride Channel Activators Identified by Screening of Combinatorial Libraries Based on Flavone and Benzoquinolizinium Lead Compounds, The Journal of Biological Chemistry, 276, 19723-19728, Mar. 21, 2001.
Brown, et al.,Chemical chaperones correct the mutant phenotype of the ΔF508 cystic fibrosis transmembrane conductance regulator . . . , (1996) Cell stress and Chaperones 1, 117-125.
Dalemans, et al., Altered chloride ion channel kinetics associated with the ΔF508 cystic fibrosis mutation, (1991), Nature 354: 526-528, vol. 354.
Denning, et al., Processing of mutant cystic fibrosis transmembrane conductance regulator is temperature-sensitive, (1992), Nature 358: 761-764, vol. 358.
Drumm, et al, Chloride conductance expressed by ΔF508 and other mutant CFTRs in *Xenopus oocytes*, (1991) Science 254:1797-1799, vol. 254.
Egan, et al., Calcium-pump inhibitors induce functional surface expression of ΔF508-CFTR protein in cystic fibrosis epithelial . . . , (2002), Nature Med. vol. 5, No. 5, 485-492.
Egan, et al.,Curcumin, a major constituent of turmeric, corrects cystic fibrosis defects, (2004) Science 304:600-602, DOI: 10.1126/science. 1093941.
Haws, et al., ΔF508-CFTR channels:kinetics, activation by forskolin, and potentiation by xanthines, (1996) Am. J. Physiol. 270, C1544-C1555.
Hwang, et al., Genistein potentiates wild-type and ΔF508-CFTR channel activity, (1997) Am. J. Physiol. 273, C988-C998.
Kang, et al., Life extension in *drosophila* by feeding a drug, (2002) Proc. Nat'l. Acad. Sci. U.S.A., vol. 99, No. 2, 838-843.
Rubenstein, et al., Sodium 4-phenylbutyrate downregulates Hsc70: implications for intracellular trafficking of ΔF508-CTFR, (2000) Am J. Physiol. 278, C259-267.
Sato, et al., Glycerol reverses the misfolding phenotype of the most common cystic fibrosis mutation, (1996) J. Biol. Chem. 271, 635-638, vol. 271, No. 2.
Sharma, et al.,Conformational and temperature-sensitive stability defects of the ΔF508 cystic fibrosis transmembrane . . . ,(2001) J. Biol. Chem., 276, 8942-8950, vol. 276, No. 12.
Wang, et al., Deletion of phenylalanine 508 causes attenuated phosphorylation-dependent activation of CFTR chloride channels, (2000) J. Physiol. 524, 637-638.

* cited by examiner

*Primary Examiner* — Golam M Shameem
(74) *Attorney, Agent, or Firm* — Carol L. Francis; Connie C. Tong; Bozicevic, Field & Francis LLP

(57) ABSTRACT

The invention provides compositions, pharmaceutical preparations and methods for increasing activity (e.g., ion transport) of the mutant cystic fibrosis transmembrane conductance regulator protein (mutant-CFTR), e.g., ΔF508 CFTR, G551D-CFTR, G1349D-CFTR, or D1152H-CFTR, that are useful for the treatment of cystic fibrosis (CF). The compositions and pharmaceutical preparations of the invention may comprise one or more phenylglycine-containing compounds or sulfonamide-containing compounds of the invention, or an analog or derivative thereof.

14 Claims, 11 Drawing Sheets

FIG. 1
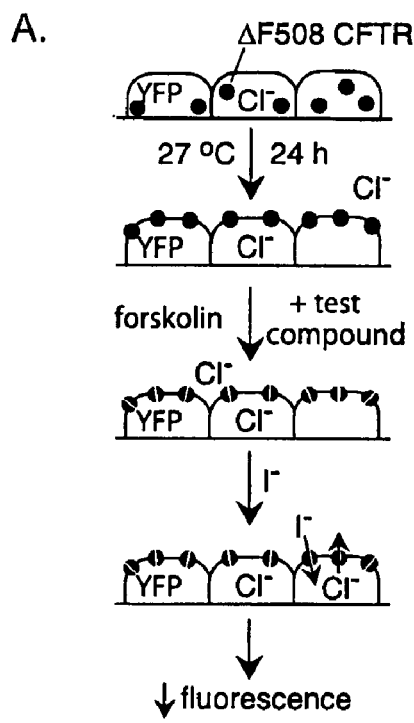
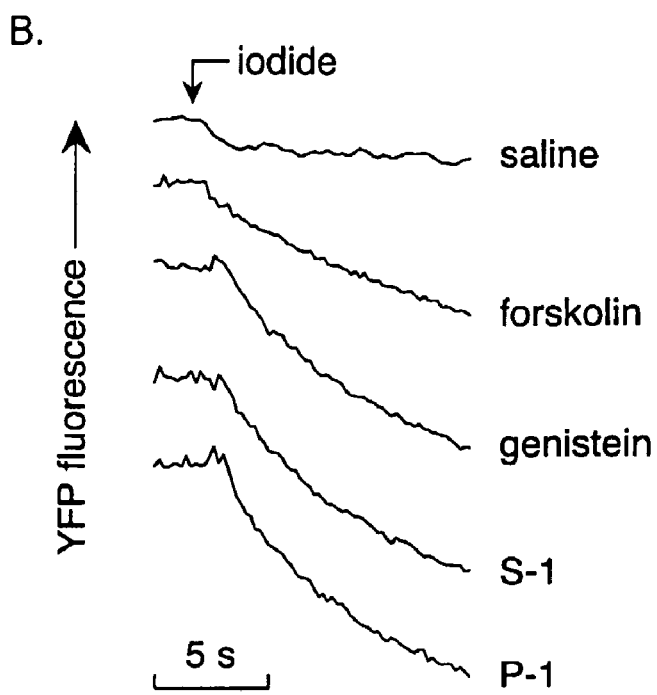

FIG. 2
A.
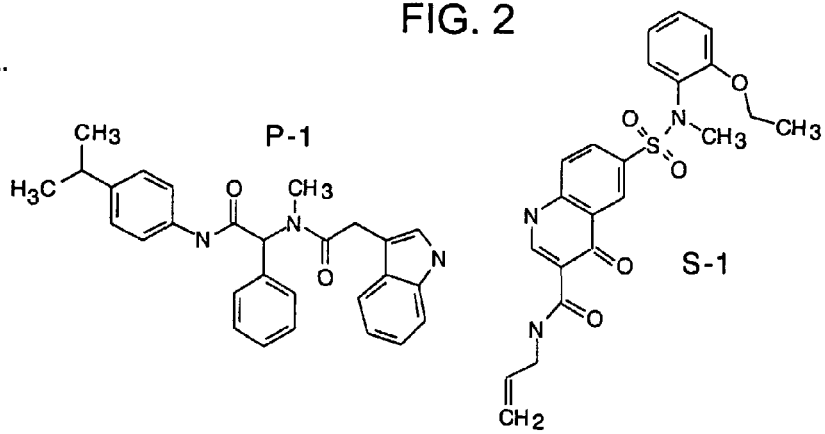
B.
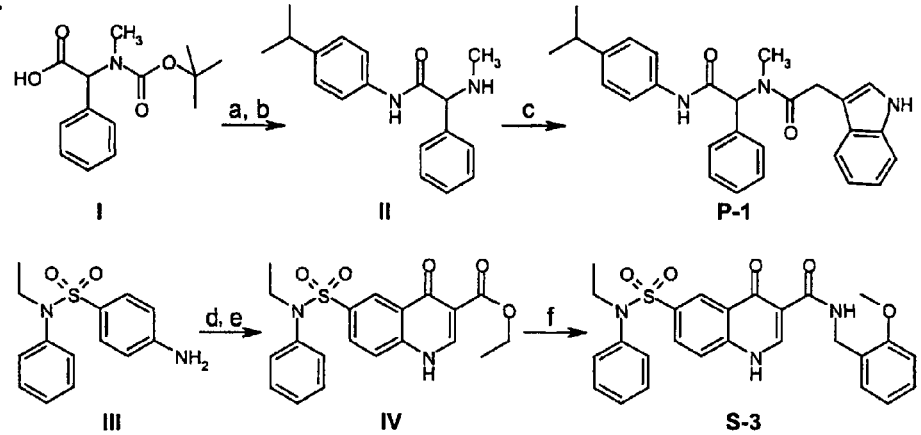
C.
Phenylglycines
4-i-Pr-Ph good;
4-Me-Ph, benzo[3,4-b][1,4]dioxane less good — R1
Me good; H, furfuryl-2-methyl less good — R3
indol-3-acetyl required — R4
H good; Me, OMe less good — R2
Sulfonamides
Well tolerated for Ph substituted with alkyl, alkoxy, halo — R1
Me, Et, 2-propenyl — R2
sulfonamide required
Well tolerated for (un)substituted/(un)branched alkyl, cycloalkyl — R3
N-Me not tolerated

COMPOUNDS HAVING ACTIVITY IN INCREASING ION TRANSPORT BY MUTANT-CFTR AND USES THEREOF

STATEMENT REGARDING FEDERALLY SPONSORED RESEARCH

This invention was made with government support under grant nos. HL73856, EB00415, HL59198, EY13574, and DK35124 awarded by the National Institutes of Health. The government may have certain rights in this invention.

Work on this invention was also supported by grants from the Cystic Fibrosis Foundation and/or from Cystic Fibrosis Foundation Therapeutics.

BACKGROUND OF THE INVENTION

The cystic fibrosis transmembrane conductance regulator protein (CFTR) is a cAMP-activated chloride ($Cl^{-1}$) channel expressed in epithelial cells in mammalian airways, intestine, pancreas and testis. CFTR is the chloride-channel responsible for cAMP-mediated $Cl^-$ secretion. Hormones, such as a β-adrenergic agonist, or toxins, such as cholera toxin, lead to an increase in cAMP, activation of cAMP-dependent protein kinase, and phosphorylation of the CFTR $Cl^-$ channel, which causes the channel to open. An increase in the concentration of $Ca^{2+}$ in a cell can also activate different apical membrane channels. Phosphorylation by protein kinase C can either open or shut $Cl^{-1}$ channels in the apical membrane. CFTR is predominantly located in epithelia where it provides a pathway for the movement of $Cl^-$ ions across the apical membrane and a key point at which to regulate the rate of transepithelial salt and water transport. CFTR chloride channel function is associated with a wide spectrum of disease, including cystic fibrosis (CF) and with some forms of male infertility, polycystic kidney disease and secretory diarrhea.

The hereditary lethal disease CF is caused by mutations in the gene encoding the CFTR protein, a cAMP-activated $Cl^-$ channel expressed in airway, intestinal, pancreatic, and other secretory and absorptive epithelia. The principal clinical problem in CF is recurrent lung infections resulting in progressive deterioration in lung function. The most common CFTR mutation, deletion of phenylalanine-508 (ΔF508-CFTR), is present in at least one allele in about 90% of CF patients (Egan et al., (2004) Science 304:600-602). ΔF508-CFTR causes $Cl^-$ impermeability because it is not processed correctly, causing it to be retained at the endoplasmic reticulum (rather than the plasma membrane). ΔF508-CFTR also has reduced intrinsic $Cl^-$ conductance relative to wild type CFTR.

Strategies have been investigated to correct the defects in ΔF508-CFTR cellular processing and intrinsic function in cells. Cell growth at low temperature (<30° C.) (Denning et al., (1992) Nature 358, 761-764) or with high concentrations of chemical chaperones such as glycerol (Sato et al., (1996) J. Biol. Chem. 271, 635-638; Brown, et al., (1996) Cell Stress & Chaperones 1, 117-125) corrects partially defective ΔF508-CFTR cellular processing by a mechanism that may involve improved protein folding and stability (Sharma et al., (2001) J. Biol. Chem. 276, 8942-8950). A sustained increase in intracellular calcium concentration by thapsigargin also corrects defective ΔF508-CFTR processing (Egan et al., (2002) Nature Med. 8, 485-492), possibly by interfering with interactions with molecular chaperones. Compounds like phenylbutyrate facilitate ΔF508-CFTR cellular processing by altering chaperone function and/or transcriptional enhancement (Rubenstein et al., (2000) Am. J. Physiol. 278, C259-C267; Kang et al., (2002) Proc. Natl. Acad. Sci. U.S.A. 99, 838-843). Although these approaches provide insight into mechanisms of ΔF508-CFTR retention at the endoplasmic reticulum, they probably do not offer clinically-useful therapies.

ΔF508-CFTR has significantly impaired channel activity even when present at the cell plasma membrane (Dalemans et al., (1991) Nature 354, 526-528). Cell-attached patch-clamp measurements showed reduced ΔF508-CFTR open channel probability and prolonged closed times even with maximal cAMP stimulation (Haws et al., (1996) Am. J. Physiol. 270, C1544-C1555; Hwang et al., (1997) Am. J. Physiol. 273, C988-C998). Patch-clamp measurements in excised membranes indicated 7-fold reduced ΔF508-CFTR activation after phosphorylation compared to wildtype CFTR. Relatively high concentrations of the flavone genistein (>50 µM, Hwang, et al., (1997) Am. J. Physiol. 273, C988-C998; Wang et al., (2000) J. Physiol. 524, 637-638) or the xanthine isobutylmethylxanthine (>1 mM, Drumm et al., (1991) Science 254, 1797-1799) in combination with cAMP agonists increase ΔF508-CFTR channel activity. Again, these studies have not offered any clinically useful therapies.

There is accordingly still a need for compounds that can activate mutant CFTR, e.g., ΔF508-CTFR G551D-CFTR, or G1349D-CFTR, and methods of using such compounds for the study and treatment of CF and the treatment and control of other secretory disorders. The present invention addresses these needs, as well as others.

SUMMARY OF THE INVENTION

The invention provides compositions, pharmaceutical preparations and methods for increasing activity (e.g., ion transport) of a mutant-cystic fibrosis transmembrane conductance regulator protein (e.g., ΔF508 CFTR, G551D-CFTR, G1349D-CFTR, or D1152H-CFTR) that are useful for the treatment of cystic fibrosis (CF). The compositions and pharmaceutical preparations of the invention may comprise one or more phenylglycine-containing compounds or sulfonamide-containing compounds of the invention, or an analog or derivative thereof.

The invention provides for a pharmaceutical composition comprising a compound of formula (I):

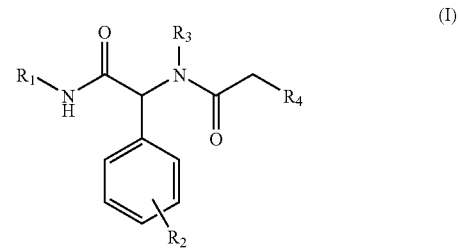

where n $R_1$ is independently chosen from a substituted or unsubstituted phenyl group or a substituted or unsubstituted heteroaromatic group, or a cyclic or acyclic alkyl group; $R_2$ is independently chosen form a hydrogen, a alkyl group, an ether group, a halogen, or a perfluoroalkyl group; $R_3$ is independently chosen from a hydrogen or an alkyl group, and $R_4$ is independently chosen from a substituted or unsubstituted heteroaromatic group, or a alkanoyl-amine group; or a pharmaceutically acceptable derivative thereof, as an individual stereoisomer or a mixture thereof; or a pharmaceutically acceptable salt thereof. In one embodiment, the composition further includes at least one of a pharmaceutically acceptable carrier, a pharmaceutically acceptable diluent, a pharmaceutically acceptable excipient and a pharmaceutically acceptable adjuvant. In another embodiment the composition does not contain detectable dimethyl sulfoxide. In preferred embodiments, the compound is chosen from: 2-[(2-1H-Indol-3-yl-acetyl)-methyl-amino]-N-(4-isopropyl-phenyl)-2-phenyl-acetamide; 2-[(2-1H-Indol-3-yl-acetyl)-methyl-amino]-N-(4-isopropyl-phenyl)-2-(4-methoxy-phenyl)-acetamide; 2-[(2-1H-Indol-3-yl-acetyl)-methyl-amino]-N-(4-methoxy-phenyl)-2-phenyl-acetamide; 2-[(2-1H-Indol-3-yl-acetyl)-methyl-amino]-2,N-bis-(4-methoxy-phenyl)-acetamide; N-(2,3-Dihydro-benzo[1,4]dioxin-6-yl)-2-(2-1H-indol-2-yl-acetylamino)-2-p-tolyl-acetamide; N-(2,3-Dihydro-benzo[1,4]dioxin-6-yl)-2-[(2-1H-indol-3-yl-acetyl)-methyl-amino]-2-(4-methoxy-phenyl)-acetamide; 2-(2-1H-Indol-3-yl-acetylamino)-N-(4-isopropyl-phenyl)-2-phenyl-acetamide; N-Benzo[1,3]dioxol-5-yl-2-[(2-1H-indol-3-yl-acetyl)-methyl-amino]-2-p-tolyl-acetamide; or 2-[(2-Acetylamino-acetyl)-methyl-amino]-N-(2,3-dihydro-benzo[1,4]dioxin-6-yl)-2-phenyl-acetamide.

In one embodiment $R_1$ is chosen from a phenyl group substituted by a hydrogen, a methyl group, an isobutanyl group, or a methoxyl group. In another embodiment, $R_2$ is chosen from a hydrogen, a methyl group, or a methoxyl group. In yet another embodiment $R_3$ is chosen from a hydrogen or a methyl group. In yet another embodiment, $R_4$ is chosen from an indole group or an alkanoylamino group.

In another embodiment of particular interest, $R_1$ is independently chosen from a substituted or unsubstituted heteroaromatic group; $R_2$ is independently chosen form a hydrogen, a alkyl group, or an ether group; $R_3$ is independently chosen from a hydrogen or an alkyl group, and $R_4$ is independently chosen from a substituted or unsubstituted heteroaromatic group, or a alkanoylamino group. In one embodiment, $R_6$ is a 2,3-dihydro-benzo[1,4]dioxine group. In another embodiment, $R_2$ is chosen from a hydrogen, a methyl group, or a methoxyl group. In yet another embodiment, $R_3$ is chosen from a hydrogen or a methyl group. In yet another embodiment, $R_4$ is chosen from an indole group or an acetylamino group.

The invention also provides for a pharmaceutical composition comprising a compound of formula (II):

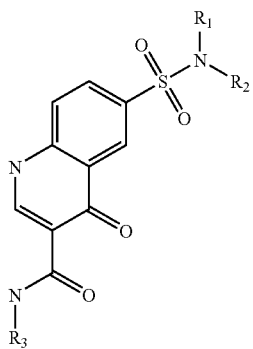

(II)

wherein $R_1$ is independently chosen form a hydrogen, an alkyl group unsubstituted or substituted by an alkoxy group; $R_2$ is independently chosen from a hydrogen or a substituted or unsubstituted phenyl group; $R_3$ is independently selected from an alkyl group unsubstituted or substituted by an alkoxy group, a substituted or unsubstituted hydrocarbon cyclic ring group, or a substituted or unsubstituted heterocyclic ring; or a pharmaceutically acceptable derivative thereof, as an individual stereoisomer or a mixture thereof; or a pharmaceutically acceptable salt thereof. In some embodiments the composition further includes at least one of a pharmaceutically acceptable carrier, a pharmaceutically acceptable diluent, a pharmaceutically acceptable excipient and a pharmaceutically acceptable adjuvant.

In one embodiment, the composition does not contain detectable dimethyl sulfoxide. In another embodiment, $R_1$ is chosen from a hydrogen, a phenyl group, a 3-fluorophenyl, a 3-methylphenyl group, a 2-methylphenyl group, a 2,6-dimethylphenyl group, or a 2-ethoxyphenyl group. In another embodiment, $R_2$ is chosen from a methyl group, an ethyl group, or a propylene group. In yet another embodiment, $R_3$ is chosen from a butyl group, a propylene group, an isopentyl group, a methoxy-propane group, a cyclopentyl group, a cylcohexyl group, a 2-methyl-furan group, or a 2-methyl-tetrahydro-furan group.

In an embodiment of particular interest the compound of formula (II) is a compound of formula (IIa):

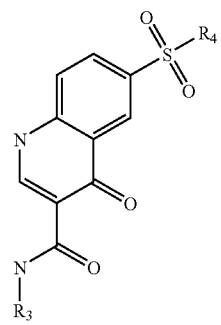

(IIa)

wherein $R_4$ is a substituted or unsubstituted heterocycloalkyl group containing a nitrogen atom, wherein the heterocycloalkyl group is linked to the sulfur atom by the nitrogen atom of the heterocycloalkyl group, a substituted or unsubstituted heterocyclic group; $R_3$ is independently selected from an alkyl group unsubstituted or substituted by an alkoxy group, a substituted or unsubstituted hydrocarbon cyclic ring group, or a substituted or unsubstituted heterocyclic ring. In an embodiment, $R_4$ is chosen from a 1,4-Dioxa-8-aza-spiro[4.5]decane group or a 2,3-Dihydro-1H-indole group. In another embodiment, $R_3$ is chosen from a butyl group, a propylene group, an isopentyl group, a 3-methoxy-propyl group, a cyclopentyl group, a cylcohexyl group, a 2-methyl-furan group, or a 2-methyl-tetrahydrofuran group. In preferred embodiments, the compound is chosen from: 6-[(2-Ethoxy-phenyl)-methyl-sulfamoyl]-4-oxo-1,4-dihydro-quinoline-3-carboxylic acid allylamide; 6-(Ethyl-phenyl-sulfamoyl)-4-oxo-1,4-dihydro-quinoline-3-carboxylic acid (3-methoxy-propyl)-amide; 6-(Methyl-m-tolyl-sulfamoyl)-4-oxo-1,4-dihydro-quinoline-3-carboxylic acid (pyridin-2-ylmethyl)-amide; 6-(Methyl-m-tolyl-sulfamoyl)-4-oxo-1,4-dihydro-quinoline-3-carboxylic acid (2-cyclohex-1-enyl-ethyl)-amide; 6-(1,4-Dioxa-8-aza-spiro[4.5]decane-8-sulfonyl)-4-oxo-1,4-dihydro-quinoline-3-carboxylic acid (3-methyl-butyl)-amide; 6-[Ethyl-(4-fluoro-phenyl)-sulfamoyl]-4-oxo-1,4-dihydro-quinoline-3-carboxylic acid cyclopentylamide; 6-(Methyl-o-tolyl-sulfamoyl)-4-oxo-1,4-dihydro-quinoline-3-carboxylic acid (3-methyl-butyl)-amide; 6-[(2,6-Dimethyl-phenyl)-methyl-sulfamoyl]-4-oxo-1,4-dihydro-quinoline-3-carboxylic acid butylamide; 6-(Allyl-phenyl-sulfamoyl)-4-oxo-1,4-dihydro-quinoline-3- carboxylic acid (furan-2-ylmethyl)-amide; 6-[Ethyl-(4-fluoro-phenyl)-sulfamoyl]-4-oxo-1,4-dihydro-quinoline-3-carboxylic acid (tetrahydro-furan-2-ylmethyl)-amide; 6-(Methyl-m-tolyl-sulfamoyl)-4-oxo-1,4-dihydro-quinoline-3-carboxylic acid sec-butylamide; or 6-(2,3-Dihydro-indole-1-sulfonyl)-4-oxo-1,4-dihydro-quinoline-3-carboxylic acid cyclohexylamide.

The invention also provides for a method of treating a subject having a condition associated with mutant-CFTR, the method including administering to the subject a therapeutically effective amount of a compound selected from the compounds of the present invention. In some embodiments, the condition is cystic fibrosis. In some embodiments the subject, after treatment, has a decrease in mucous or bacterial titer in their lungs, a decrease in coughing or wheezing, a decrease in pancreatic insufficiency, or a decrease in electrolyte levels in their sweat. In some embodiments the subject is a non-human animal. In embodiments of particular interest the animal is a mammal. In some embodiments the mutant-CFTR is ΔF508-CFTR, G551D-CFTR, G1349D-CFTR, or D1152H-CFTR.

The invention also provides for a method of increasing ion permeability of a cell producing a mutant-CFTR protein, the method including contacting the cell with a compound in an amount effective to increase ion permeability of said cell, wherein the compound is selected from the compounds of the present invention. In some embodiments the cell contains a recombinant expression cassette that encodes said mutant-CFTR protein. In other embodiments the cell contains a genome that encodes said mutant-CFTR protein. In yet other embodiments the ion permeability increases an ion transporting activity that increases a rate of transport of ions across the plasma membrane of said cell. In yet other embodiments the mutant-CFTR is ΔF508-CFTR, G551D-CFTR, G1349D-CFTR, or D1152H-CFTR.

These and other objects and advantages of the invention will be apparent from the detailed description below.

BRIEF DESCRIPTION OF THE DRAWINGS

The invention will be more fully understood by reference to the following drawings, which are for illustrative purposes only.

FIG. 1 shows the details of identification of the subject compounds. Panel A is a schematic representation of a high-throughput screening procedure used in the subject methods. Cells co-expressing mutant-CFTR and the halide-sensitive fluorescent protein YFP-H148Q/I152L were grown for 24 h at 27° C. (to give plasma membrane mutant-CFTR expression). After washing, test compounds (2.5 μM) and forskolin (20 μM) were added, and I$^-$ influx was assayed from the time course of YFP-H148Q/152L fluorescence after adding I$^-$ to the external solution. Panel B shows the original traces showing quenching of cellular YFP fluorescence by I$^-$ addition with saline alone, and after additions of forskolin (20 μM) alone, or forskolin plus genistein (50 μM), compound S-1 (2.5 μM) or compound P-1 (2.5 μM).

FIG. 2 shows the synthesis and structure activity analysis of the subject compound. Panel A shows the structures of an exemplary phenylglycine containing compound (denoted as P-1) and an exemplary sulfonamide containing compound (denoted as S-1). Panel B, top portion, shows the synthesis of the phenylglycine containing compound P-1. Conditions: a. p-isopropylaniline, EDCI, cat. (catalytic amount) DMAP, CH$_2$Cl$_2$, 22° C., 2 h, yield 92%; b. TFA, 22° C., 15 min, 98%; c. indole-3-acetic acid, EDCI, cat. DMAP, CH$_2$Cl$_2$, 22° C., 2 h, 92%. Panel A, bottom portion, shows the synthesis of the sulfonamide containing compound S-3. Conditions: d. diethyl ethoxymethylene-malonate, 140° C., 1 h, 95%; e. cat. p-chlorobenzoic acid. Ph$_2$O, 250° C., 45%; f. o-methoxybenzyl-amine, neat, 180° C., 35%. Panel C shows the conclusions from structure-activity relationship analysis of the phenylglycine containing compounds and the sulfonamide containing compounds.

Figure 3:
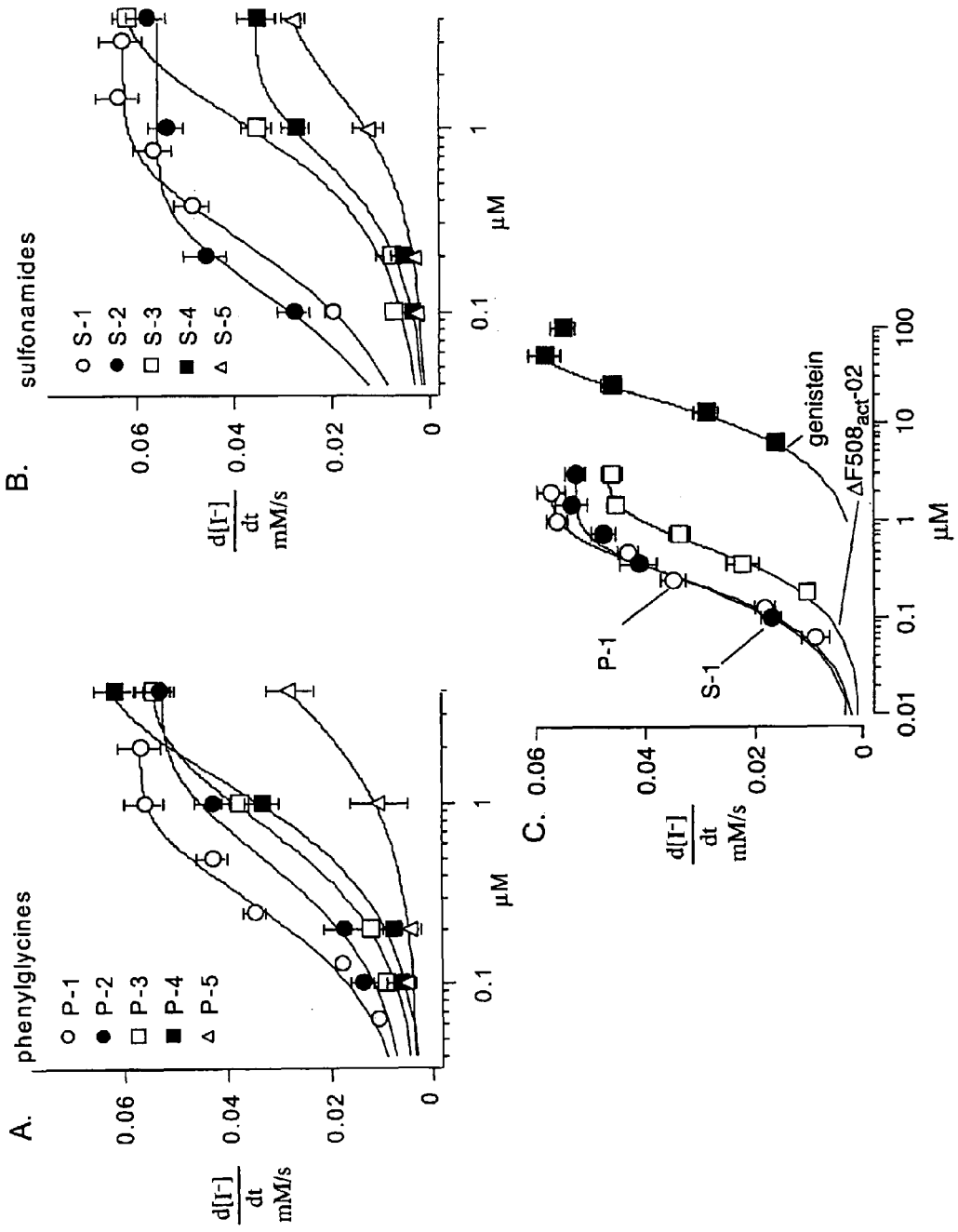
FIG. 3 provides dose response analysis of the subject compounds. Panel A is a graph showing I$^-$ influx rates (d[I$^-$]/dt) for phenylglycine containing compounds. Panel B is a graph showing I$^-$ influx rates (d[I$^-$]/dt) for sulfonamide containing compounds. Panel C is a graph showing I$^-$ influx rates (d[I$^-$]/dt) for the indicated compounds (mean±SE, n=4), including the tetrahydrobenzothiophene ΔF508$_{act}$-02 (Yang et. al., JBC 278:35079-35085 (2003)).

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It should be noted that, as used herein and in the appended claims, the singular forms "a", "and", and "the" include plural referents unless the context clearly dictates otherwise. Thus, for example, reference to "a compound" includes a plurality of such compounds, and reference to "the cell" includes reference to one or more cells and equivalents thereof known to those skilled in the art, and so forth.

The publications discussed herein are provided solely for their disclosure prior to the filing date of the present application, and are incorporated herein by reference. Nothing herein is to be construed as an admission that the present invention is not entitled to antedate such publication by virtue of prior invention. Further, the dates of publication provided may be different from the actual publication dates that may need to be independently confirmed.

The definitions used herein are provided for reason of clarity, and should not be considered as limiting. The technical and scientific terms used herein are intended to have the same meaning as commonly understood by those of ordinary skill in the art to which the invention pertains.

DETAILED DESCRIPTION OF THE INVENTION

The invention provides compositions, pharmaceutical preparations and methods for activation of mutant cystic fibrosis transmembrane conductance regulator protein (e.g., ΔF508-CFTR, G55 ID-CFTR, G1349D-CFTR, or D1152H-CFTR) that are useful for the study and treatment of cystic fibrosis (CF). The invention also features methods of use of such compositions in increasing activity of mutant CFTR in a cell, e.g., by increasing ion transport by mutant CFTR.

In one embodiment, the compositions and pharmaceutical preparations of the invention may comprise one or more compounds, which compounds can be a phenylglycine containing compound, or an analog or derivative thereof, and a sulfonamide containing compound, or an analog or derivative thereof. The compositions and pharmaceutical preparations of the invention may additionally comprise one or more pharmaceutically acceptable carriers, excipients and/or adjuvants.

The invention provides methods of increasing ion transport in a mutant-CFTR, e.g., ΔF508-CFTR G551D-CFTR, G1349D-CFTR, or D1152H-CFTR, in a cell by contacting the cell with an effective amount of one or more of the compounds set forth above. In other embodiments, the invention also provides a method of treating a patient suffering from a mutant-CFTR-mediated disease or condition, for example CF, by administering to the patient an efficacious amount of one or more of the compounds set forth above. Kits for use in the subject methods are also provided.

In one aspect of particular interest, the invention is based on the discovery of a genus of phenylglycine containing compounds that increase ion transport by mutant-CFTR with high affinity.

In another aspect of particular interest, the invention is based on the discovery of a genus of sulfonamide containing compounds that increase ion transport by mutant-CFTR with high affinity.

In describing the invention, the structure of the compounds of the invention will be described first. Then, pharmaceutical formulations containing the compounds will be discussed, followed by a description of their methods of use.

Definitions

A "mutant cystic fibrosis transmembrane conductance regulator protein", or "mutant-CFTR" is the protein that results from a mutation, e.g., deletion mutation, insertion mutation, or point (substitution) mutation of the CFTR gene product relative to wildtype. As used herein a "mutant cystic fibrosis transmembrane conductance regulator protein", or "mutant-CFTR" is dysfunctional as compared to a functional (e.g., wildtype) CFTR where the dysfunction can encompass one or more of the following: (i) aberrant CFTR production (e.g., at the level of transcription or translation); (ii) aberrant folding and/or trafficking; (iii) abnormal regulation of conductance; (iv) decreases in chloride conductance; (v) reduction in synthesis; and the like. A "mutant-CFTR gene" is a gene, or coding sequence, which encodes a mutant-CFTR. For the purposes of this application, the terms "genome" and "gene" are used interchangeably, e.g. "genome that encodes mutant-CFTR" and "gene that encodes mutant-CFTR".

A "gating defective mutant cystic fibrosis transmembrane conductance regulator protein", or "gating defective mutant-CFTR" is a mutant-CFTR that is present on the cell surface and is defective in gating of ions through the channel (e.g., regulation of ion transport). Thus, as used herein a "gating defective mutant-CFTR" encompasses dysfunctions associated with (i) abnormal regulation of conductance; and or (ii) decreases in chloride conductance.

A "mutant-CFTR protein-mediated condition" means any condition, disorder or disease, or symptom of such condition, disorder, or disease, that results from or is correlated to the presence of a mutant-CFTR, e.g., ΔF508-CFTR, e.g., chloride ion impermeability caused by reduced activity of ΔF508-CFTR in ion transport relative to a wild-type CFTR. A "mutant-CFTR protein-mediated condition" encompasses conditions in an affected subject which are associated with the presence of a ΔF508-CFTR mutation on at least one allele, thus including subjects that carry a ΔF508-CFTR mutation on both alleles as well as compound heterozygous subjects having two different mutant forms of CFTR, e.g., a subject with one copy of ΔF508-CFTR and a copy of different mutant form of CFTR.

Such conditions, disorders, diseases, or symptoms thereof are treatable by specific activation of mutant-CFTR activity, e.g., activation of mutant-CFTR ion transport. ΔF508-CFTR is correlated to the presence of cystic fibrosis (CF), and a description of this disease, including its symptoms, is found in Accession No. 602421 (entitled cystic fibrosis transmembrane conductance regulator; CFTR), and Accession No. 219700 (entitled Cystic fibrosis; CF) of the Online Mendelian Inheritance of Man database, as found at the world wide website of the National Institute of Health at ncbi.nlm.nih.gov. Symptoms of mutant-CFTR protein-mediated conditions include meconium ileus, liver disease including biliary tract obstruction and stenosis, pancreatic insufficiency, pulmonary disease including chronic *Pseudomonas aeruginosa* infections and other infections of the lung, infertility associated with abnormal vas deferens development or abnormal cervical mucus, and carcinoma including adenocarcinoma. Many subjects that have a mutant-CFTR protein-mediated condition are homozygous for a gene encoding a ΔF508-CFTR protein.

A "ΔF508-cystic fibrosis transmembrane conductance regulator protein", or "ΔF508-CFTR" is the protein that results from the deletion of a phenylalanine residue at amino acid position 508 of the CFTR gene product. A "ΔF508-CFTR gene" is a gene, or coding sequence, which encodes ΔF508-CFTR. A ΔF508-CFTR gene usually results from deletion of three nucleotides corresponding to the phenylalanine residue at amino acid position 508 of the encoded CFTR gene product. For the purposes of this application, the terms "genome" and "gene" are used interchangeably, e.g. "genome that encodes ΔF508-CFTR" and "gene that encodes ΔF508-CFTR". For an example of a gene that encodes ΔF508-CFTR, see, e.g. WO 91/02796.

A "mutant-CFTR activator" as used herein is a compound that increases the level of ion transport by a mutant-CFTR relative to ion transport in the absence of the compound, and particularly with respect to transport of chloride ions. CFTR activators of the invention of particular interest are those that are specific mutant-CFTR activators, e.g., compounds that activate mutant-CFTR activity rather than affecting CFTR cellular misprocessing. Mutant-CFTR activators are usually high-affinity mutant-CFTR activators, e.g., have an affinity for mutant-CFTR of at least about one micromolar, about one to five micromolar, about 200 nanomolar to one micromolar, about 50 nanomolar to 200 nanomolar, or below 50 nanomolar.

A "gating defective mutant-CFTR activator" as used herein is a compound that increases the level of ion transport by a gating defective mutant-CFTR relative to ion transport in the absence of the compound, and particularly with respect to transport of chloride ions. CFTR activators of the invention of particular interest are those that are specific gating defective mutant-CFTR activators, e.g., compounds that activate gating defective mutant-CFTR activity rather than affecting, for example, CFTR cellular misprocessing. Gating defective mutant-CFTR activators are usually high-affinity activators of gating defective mutant-CFTRs, e.g., have an affinity for a gating defective mutant-CFTR (e.g., ΔF508-CFTR, G551D-CFTR, G1349D-CFTR, or D1152H-CFTR) of at least about one micromolar, about one to five micromolar, about 200 nanomolar to one micromolar, about 50 nanomolar to 200 nanomolar, or below 50 nanomolar.

A "ΔF508-CFTR activator" as used herein is a compound that increases the level of ion transport by ΔF508-CFTR relative to ion transport in the absence of the compound, and particularly with respect to transport of chloride ions. CFTR activators of the invention of particular interest are those that are specific ΔF508-CFTR activators, e.g., compounds that activate ΔF508-CFTR activity rather than affecting CFTR cellular misprocessing. ΔF508-CFTR activators are usually high-affinity ΔF508-CFTR activators, e.g., have an affinity for ΔF508-CFTR of at least about one micromolar, about one to five micromolar, about 200 nanomolar to one micromolar, about 50 nanomolar to 200 nanomolar, or below 50 nanomolar.

As used herein and in the cystic fibrosis field a "potentiator" refers to a compound that increases a basal level of ion transport by a mutant-CFTR (e.g., ΔF508CFTR, G551 D-CFTR, G1349D-CFTR, or D1152H-CFTR), where the mutant CFTR (in the absence of the compound) exhibits aberrantly low levels of ion transport relative to wildtype CFTR. As such, a "mutant-CFTR potentiator" refers to a potentiator compound that, provides for increased level of ion transport by a mutant-CFTR relative to ion transport capability of the mutant-CFTR in the absence of the compounds.

As used herein and in the cystic fibrosis field a "mutant-CFTR corrector" is a compound that increases the level of ion transport by a mutant-CFTR relative to ion transport in the absence of the compound by correcting the underlying defect of the CFTR polypeptide, e.g., a defect that results from post-translational mis-processing (e.g., misfolding). CFTR correctors of the invention of particular interest are those that facilitate correction of specific mutant-CFTRs. Mutant-CFTR correctors are usually exhibit high-affinity for one or more mutant-CFTRs, e.g., have an affinity for mutant-CFTR of at least about one micromolar, about one to five micromolar, about 200 nanomolar to one micromolar, about 50 nanomolar to 200 nanomolar, or below 50 nanomolar.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

The term "isolated compound" means a compound which has been substantially separated from, or enriched relative to, other compounds with which it occurs in nature. Isolated compounds are usually at least about 80%, more usually at least 90% pure, even more preferably at least 98% pure, most preferably at least about 99% pure, by weight. The present invention is meant to comprehend diastereomers as well as their racemic and resolved, enantiomerically pure forms and pharmaceutically acceptable salts thereof.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

The terms "subject" and "patient" mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound (e.g., phenylglycine-containing compound or sulfonamide containing compound) employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like. In some embodiments the composition is suitable for administration by a transdermal route, using a penetration enhancer other than DMSO. In other embodiments, the pharmaceutical compositions are suitable for administration by a route other than transdermal administration.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutically acceptable ester" of a compound of the invention means an ester that is pharmaceutically acceptable and that possesses the desired pharmacological activity of the parent compound, and includes, but is not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

A "pharmaceutically acceptable enol ether" of a compound of the invention means an enol ether that is pharmaceutically acceptable and that possesses the desired pharmacological activity of the parent compound, and includes, but is not limited to, derivatives of formula C=C(OR) where R is hydrogen, alkyl, alkenyl, alkynyl, aryl, heteroaryl, aralkyl, heteroaralkyl, cycloalkyl or heterocyclyl.

A "pharmaceutically acceptable enol ester" of a compound of the invention means an enol ester that is pharmaceutically acceptable and that possesses the desired pharmacological activity of the parent compound, and includes, but is not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

"Pro-drugs" means any compound that releases an active parent drug according to formula (I) in vivo when such pro-drug is administered to a mammalian subject. Prodrugs of a compound of formula (I) are prepared by modifying functional groups present in the compound of formula (I) in such a way that the modifications may be cleaved in vivo to release the parent compound. Prodrugs include compounds of formula (I) wherein a hydroxy, amino, or sulfhydryl group in compound (1) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of formula (I), and the like.

The term "organic group" and "organic radical" as used herein means any carbon-containing group, including hydrocarbon groups that are classified as an aliphatic group, cyclic group, aromatic group, functionalized derivatives thereof and/or various combination thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, iso-propyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, triflorom-ethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo" and "halogen" refer to the fluoro, chloro, bromo or iodo groups. There can be one or more halogen, which are the same or different. Halogens of particular interest include chloro and bromo groups.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl) hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(isopropyl)phenyl, 2, 3, or 4-ethylphenyl, 2, 3 or 4-(n-propyl) phenyl and the like; a mono or di(alkoxy)phenyl group, for example, 2,6-dimethoxyphenyl, 2,3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl)ethyl, 4-(2',6'-dihydroxy phenyl)n-hexyl, 2-(5'-cyano-3'-methoxyphenyl)$_n$-pentyl, 3-(2',6'-dimethylphenyl)$_n$-propyl, 4-chloro-3-aminobenzyl, 6-(4'-methoxyphenyl)-3-carboxy(n-hexyl), 5-(4'-aminomethylphenyl)-3-(aminomethyl)$_n$-pentyl, 5-phenyl-3-oxo-n-pent-1-yl, (4-hydroxynapth-2-yl)methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $_C$4 alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

Overview

The invention provides compounds that increase ion transport in a mutant-cystic fibrosis transmembrane conductance regulator protein (mutant-CFTR), e.g., ΔF508-CFTR, G551D-CFTR, G1349D-CFTR, or D1152H-CFTR, and methods of their use in treatment of mutant-CFTR-mediated diseases and conditions, e.g., cystic fibrosis (CF). Such compounds find use in the study of CFTR ion transport, particularly that of ΔF508-CFTR G551 D-CFTR, G1349D-CFTR, and D1152H-CFTR.

In one embodiment, the invention provides high-affinity small-molecule compounds that increase Cl⁻ conductance in gating defective mutant-CFTRs, such as ΔF508-CFTR, G551D-CFTR, G1349D-CFTR, and D1152H-CFTR. The compounds contemplated by the invention include those of the following structural classes: (1) phenylglycine containing compounds; and (2) sulfonamide containing compounds.

The discovery of the subject compounds was based on screening of numerous candidate compounds using an assay designed to identify mutant-CFTR activating compounds. A screening of 50,000 diverse compounds identified several compounds and analogs as effective mutant-CFTR potentiators. The subject compounds are unrelated chemically and structurally to previously known mutant-CFTR potentiator compounds.

As such the invention provides compounds that increase ion transport mediated by mutant-CFTR. Without wishing to be bound by this theory, it is speculated, with respect to the ΔF508-CFTR, that the compounds act through direct interaction or binding mechanism with ΔF508-CFTR, most likely to a site on the first nucleotide binding domain of CFTR where the ΔF508 mutation site is located.

The compositions and methods of the invention will now be described in more detail.

Compositions

Phenylglycine Containing Compounds

The phenylglycine containing compounds describe herein comprise an aromatic- or heteroaromatic nitrogen, a substituted or unsubstituted phenyl glycine and a substituted or unsubstituted aryl group or a carbonyl group. In specific embodiments, the subject compounds are generally described by Formula (I) as follows:

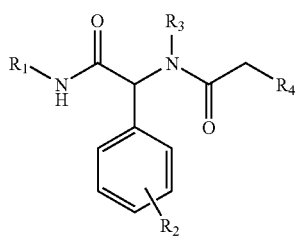
(I)

where n $R_1$ is independently chosen from a substituted or unsubstituted phenyl group or a substituted or unsubstituted heteroaromatic group; $R_2$ is independently chosen form a hydrogen, a alkyl group, or an ether group; $R_3$ is independently chosen from a hydrogen or an alkyl group, and $R_4$ is independently chosen from a substituted or unsubstituted heteroaromatic group; or a pharmaceutically acceptable derivative thereof, as an individual stereoisomer or a mixture thereof. In one embodiment, $R_1$ is independently chosen from an unsubstituted heteroaromatic group or a substituted phenyl group; $R_2$ is independently chosen from a hydrogen, a alkyl group, or an ether group; $R_3$ is independently chosen from a hydrogen or an alkyl group; and $R_4$ is independently chosen form a unsubstituted heteroaromatic group or a or a isopropenylamine group. Exemplary substitutions for $R_1$, $R_2$, $R_3$, and $R_4$ are described in more detail below.

In certain embodiments, the phenylglycine containing compounds are generally described by Formula (I), wherein $R_1$ is a substituted phenyl group. Such compounds are generally described by Formula (Ia) as follows:

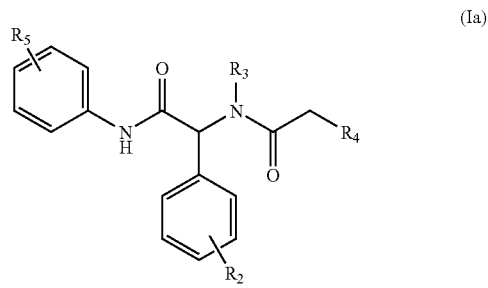
(Ia)

wherein $R_5$ is independently chosen from a hydrogen, an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl, or an ether group, such as a methoxyl group or an ethoxyl group; $R_2$ is independently chosen from a hydrogen, an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl, or an ether group, such as a methoxyl group or an ethoxyl group; and $R_3$ is independently chosen from a substituted or unsubstituted heteroaromatic group, such as an indole group; and $R_4$ is independently chosen form a unsubstituted heteroaromatic group or a isopropenylamine group.

In specific embodiments, $R_5$ is independently chosen from a hydrogen, a methyl group, an isobutanyl group, or a methoxyl group; $R_2$ is independently chosen from a hydrogen, a methyl group, or a methoxyl group; $R_3$ is independently chosen from a hydrogen or a methyl group; and $R_4$ is independently chosen from an indole group or a isopropenylamine group.

In certain embodiments, the phenylglycine containing compounds are generally described by Formula (I), wherein $R_1$ is a heteroaryl group. Such compounds are generally described by Formula (Ib) as follows:

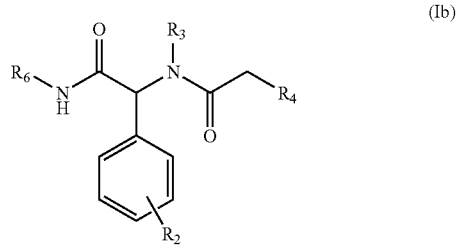
(Ib)

wherein $R_6$ is independently chosen from a substituted or unsubstituted heteroaromatic group, such as a dihydro-benzodioxine group, such as a 2,3-dihydro-benzo[1,4]dioxine group; $R_2$ is independently chosen from a hydrogen, an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl, or an ether group, such as a methoxyl group or an ethoxyl group; $R_3$ is independently chosen from a substituted or unsubstituted heteroaromatic group, such as an indole group; and $R_4$ is independently chosen form a unsubstituted heteroaromatic group or a isopropenylamine group.

In specific embodiments, $R_6$ is a 2,3-dihydro-benzo[1,4] dioxine group; $R_2$ is independently chosen from a hydrogen, a methyl group, or a methoxyl group; $R_3$ is independently chosen from a hydrogen or a methyl group; and $R_4$ is independently chosen from an indole group or a isopropenylamine group.

In some embodiments of the invention, the phenylglycine containing compounds may comprise a formula of the following:

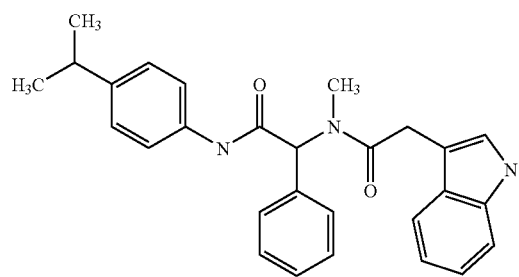

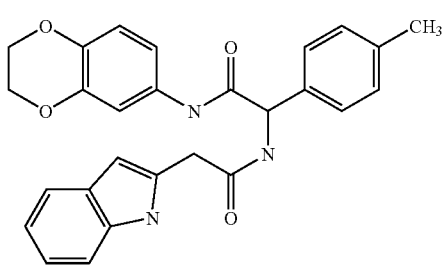

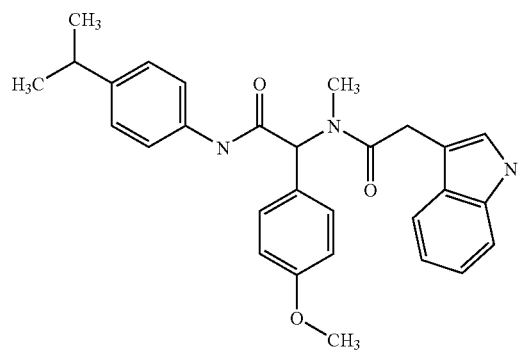

-continued

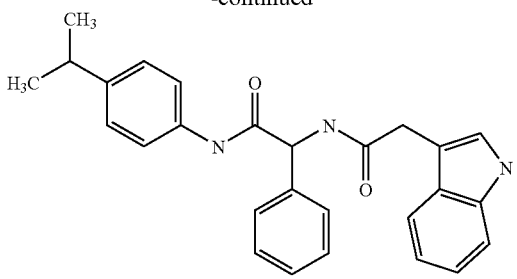

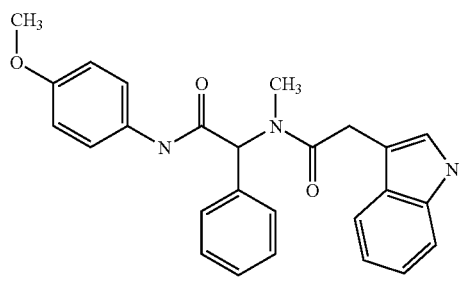

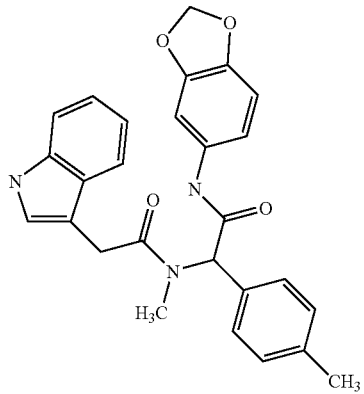

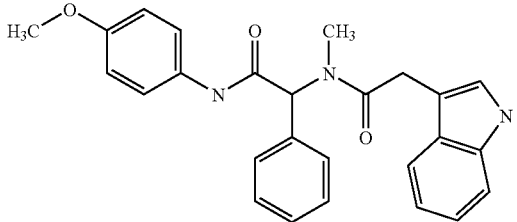

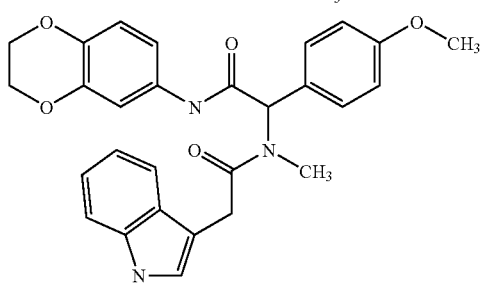

-continued

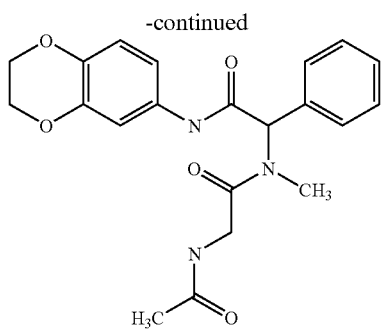

Sulfonamide Containing Compounds

The sulfonamide containing compounds described herein comprise a substituted sulfonamide, a substituted heteroaromatic group, and a substituted formamide. In specific embodiments, the subject compounds are generally described by Formula (II) as follows:

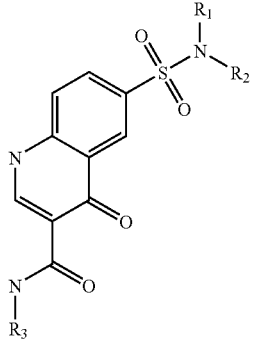

(II)

wherein $R_1$ is independently chosen form a hydrogen, an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl, or an ether group, such as a methoxyl group or an ethoxyl group; $R_2$ is independently chosen from a hydrogen or a substituted or unsubstituted phenyl group; $R_3$ is independently selected from a an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl, an ether group, a substituted or unsubstituted hydrocarbon cyclic ring group, or a substituted or unsubstituted heterocyclic ring; or a pharmaceutically acceptable derivative thereof, as an individual stereoisomer or a mixture thereof. In one embodiment, $R_1$ is independently chosen from a hydrogen or an alkyl group; $R_2$ is independently chosen form a substituted or unsubstituted phenyl group; R3 is independently selected from a substituted or unsubstituted alkyl group, a substituted or unsubstituted hydrocarbon cyclic ring group, a substituted or -unsubstituted (heteroaryl)alkyl group, a substituted or unsubstituted (cycloalkyl)alkyl group, or a substituted or unsubstituted (heterocycloalkyl)alkyl group. Exemplary substitutions for $R_1$, $R_2$, and $R_3$ are described in more detail below.

In specific embodiments, $R_1$ is independently chosen form a hydrogen; an unsubstituted phenyl group; a mono- or di(halo)phenyl group such as 2-, 3-, 4-, or 5-fluorophenyl, 3,4- or 5,6- or 5,7- or 5,8-difluorophenyl; a mono- or di-(alkyl)phenyl group, such as a 2-, 3-, 4-, or 5-methylphenyl group, 2,6- or 3,4- or 5,6- or 5,7- or 5,8-dimethylphenyl; or a mono (alkoxy)phenyl group, such as a 2-, 3-, 4-, or 5-methoxyphenyl, 2-, 3-, 4-, or 5-ethoxyphenyl, 2-, 3-, 4-, or 5-propoxyphenyl; $R_2$ is independently selected from a alkyl group, such as a methyl group, an ethyl group, or a propylene group; $R_3$ is independently selected from a alkyl group, such as a butyl group, a propylene group, an isopentyl group, and a methoxypropane; a cycloalkyl group, such as a cyclopentane, and a cylcohexane; a (cycloalkyl)alkyl group, such as a ethyl-cyclohexene; a (heteroaromatic)alkyl group, such as a 3-methyl-furan, and a 2-, 3-, 4-, or 5-methyl-pyridine; or a (heterocycloalkyl)alkyl group, such as a 3-methyl-tetrahydro-furan group.

In certain embodiments, the sulfonamide containing compounds are generally described by Formula (II), wherein the $R_1$ and $R_2$ substituted nitrogen is a $R_4$ group. Such compounds are generally described by Formula (IIa) as follows:

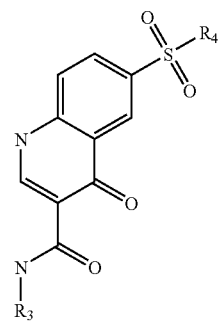

(IIa)

wherein $R_4$ is a substituted or unsubstituted heterocycloalkyl group containing a nitrogen atom, wherein the heterocycloalkyl group is linked to the sulfur atom by the nitrogen atom of the heterocycloalkyl group, a substituted or unsubstituted heterocyclic group; $R_3$ is independently selected from a an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl, an ether group, a substituted or unsubstituted hydrocarbon cyclic ring group, or a substituted or unsubstituted heterocyclic ring. Exemplary substitutions for $R_4$ and $R_3$ are described in more detail below.

In specific embodiments, $R_4$ is independently select from 1,4-Dioxa-8-aza-spiro[4.5]decane group or a 2,3-Dihydro-1H-indole group; and $R_3$ is independently selected from a alkyl group, such as a butyl group, a propylene group, an isopentyl group, and a methoxy-propane; a cycloalkyl group, such as a cyclopentane, and a cylcohexane; a (cycloalkyl)alkyl group, such as a ethyl-cyclohexene; a (heteroaromatic)alkyl group, such as a 3-methyl-furan, and a 2-, 3-, 4-, or 5-methyl-pyridine; or a (heterocycloalkyl)alkyl group, such as a 3-methyl-tetrahydro-furan group.

In some embodiments of the invention, the phenylglycine containing compounds may comprise a formula of the following:

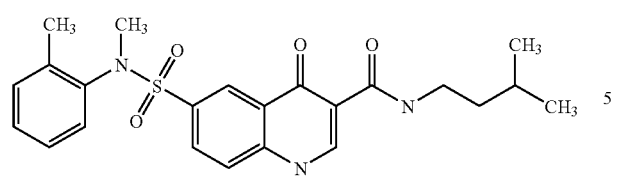
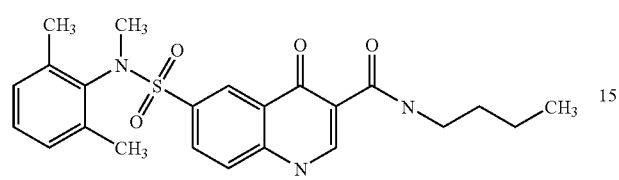
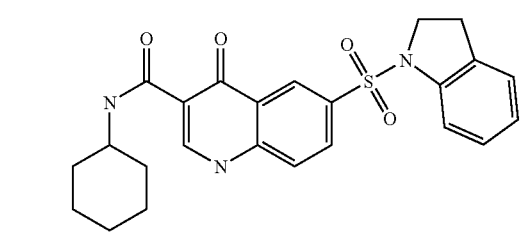
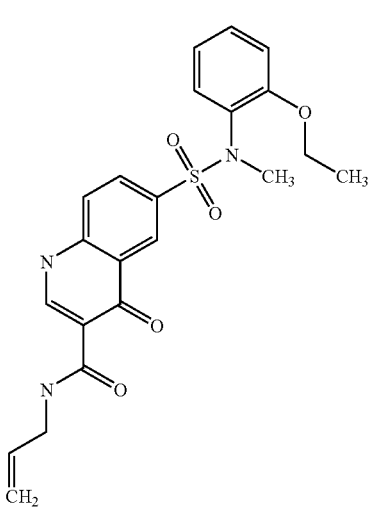
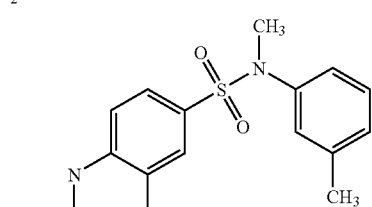
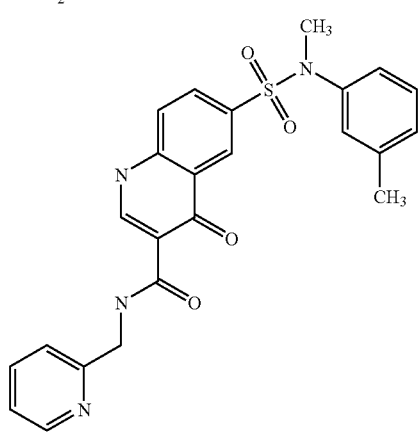
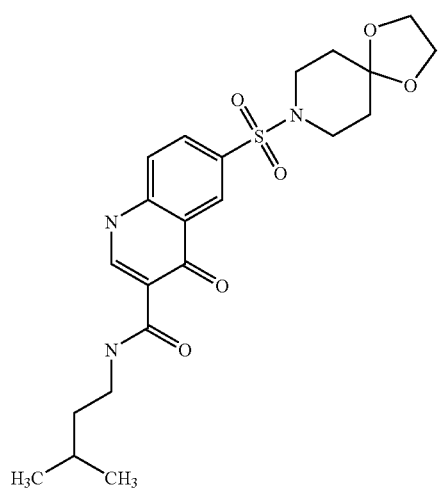
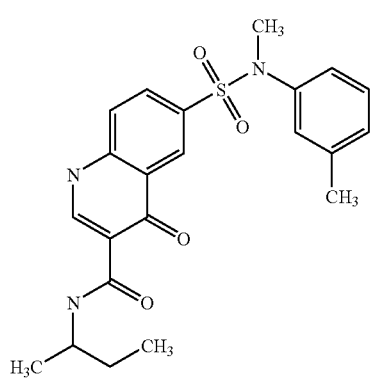
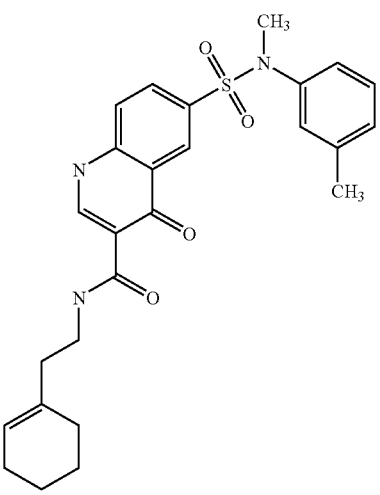

-continued

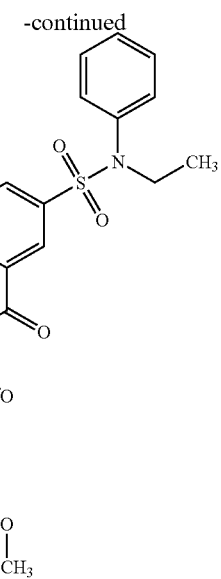

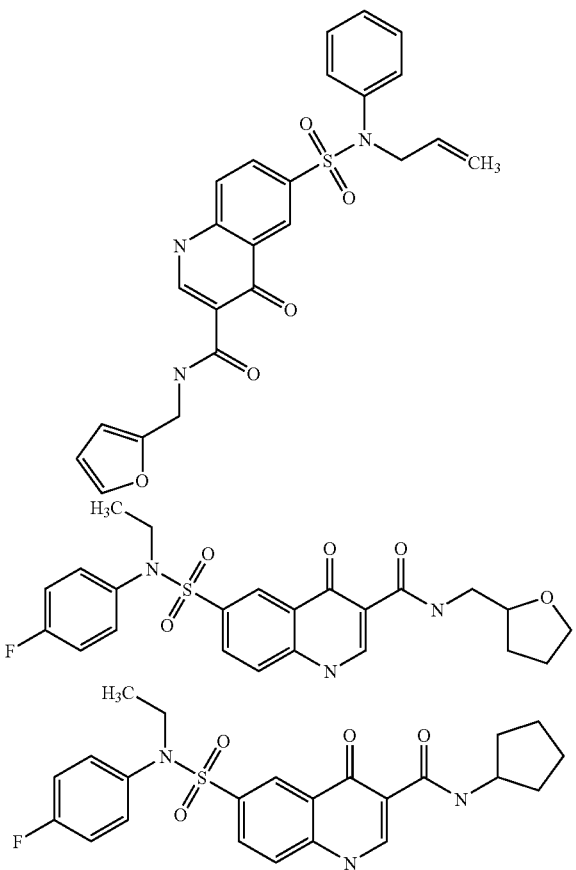

Analog and Derivative Compounds

Also provided by the invention are analogs and derivatives of the subject compounds described above. The terms "analog" and "derivative" refers to a molecule which is structurally similar or has the same function or activity as the subject phenylglycine containing compounds or sulfonamide containing compounds of the invention. Such analogs and derivatives of the subject compounds can be screened for efficiency in binding to and modulating the activity of a mutant CFTR, such as ΔF508-CFTR, G551D-CFTR, G1349D-CFTR, or D1152H-CFTR.

In some embodiments, in silico modeling can be used to screen 3-dimensional libraries of analog or derivative compounds for activity in binding to and modulating the activity of a mutant CFTR, such as ΔF508-CFTR, G551D-CFTR, G1349D-CFTR, or D1152H-CFTR. An exemplary in silico modeling program suitable for use with the subject method is the PREDICT™ 3D Modeling Technology (Predix Pharmaceuticals, Woburn Mass.), described in greater detail in Becker et al., PNAS 101(31):11304-11309 (2004).

Pharmaceutical Preparations Containing Compounds of the Invention

Also provided by the invention are pharmaceutical preparations of the subject compounds described above. The subject compounds can be incorporated into a variety of formulations for therapeutic administration by a variety of routes. More particularly, the compounds of the present invention can be formulated into pharmaceutical compositions by combination with appropriate, pharmaceutically acceptable carriers, diluents, excipients and/or adjuvants, and may be formulated into preparations in solid, semi-solid, liquid or gaseous forms, such as tablets, capsules, powders, granules, ointments, solutions, suppositories, injections, inhalants and aerosols. In most embodiments, the formulations are free of detectable DMSO (dimethyl sulfoxide), which is not a pharmaceutically acceptable carrier, diluent, excipient, or adjuvant, particularly in the context of routes of administration other than transdermal routes. Where the formulation is for transdermal administration, the compounds are preferably formulated either without detectable DMSO or with a carrier in addition to DMSO. The formulations may be designed for administration to subjects or patients in need thereof via a number of different routes, including oral, buccal, rectal, parenteral, intraperitoneal, intradermal, intratracheal, etc., administration.

Pharmaceutically acceptable excipients usable with the invention, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins. The composition or formulation to be administered will, in any event, contain a quantity of the agent adequate to achieve the desired state in the subject being treated.

Dosage Forms of Compounds of the Invention

In pharmaceutical dosage forms, the subject compounds of the invention may be administered in the form of their pharmaceutically acceptable salts, or they may also be used alone or in appropriate association, as well as in combination, with other pharmaceutically active compounds. The following methods and excipients are merely exemplary and are in no way limiting.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes, such as intrapulmonary or intranasal delivery.

Conventional and pharmaceutically acceptable routes of administration include intranasal, intrapulmonary intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

In one embodiment of particular interest, the compounds of the invention are administered in aerosol formulation via intrapulmonary inhalation. The compounds of the present invention can be formulated into pressurized acceptable propellants such as dichlorodifluoromethane, propane, nitrogen and the like.

Mechanical devices designed for intrapulmonary delivery of therapeutic products, include but are not limited to nebulizers, metered dose inhalers, and powder inhalers, all of which are familiar to those of skill in the art. Specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; the Spinhaler powder inhaler, manufactured by Fisons Corp., Bedford, Mass.; the "standing cloud" device of Inhale Therapeutic Systems, Inc., San Carlos, Calif.; the AIR inhaler manufactured by Alkennes, Cambridge, Mass.; and the AERx pulmonary drug delivery system manufactured by Aradigm Corporation, Hayward, Calif. Of particular interest are the PARI LC PLUS®, the PARI LC STAR®, and the PARI BABY™ nebulizers by PARI Respiratory Equipment, Inc., Monterey, Calif.

Formulations for use with a metered dose inhaler device may generally comprise a finely divided powder. This powder may be produced by lyophilizing and then milling a liquid conjugate formulation and may also contain a stabilizer such as human serum albumin (HSA). Typically, more than 0.5% (w/w) HSA is added. Additionally, one or more sugars or sugar alcohols may be added to the preparation if necessary. Examples include lactose maltose, mannitol, sorbitol, sorbitose, trehalose, xylitol, and xylose. The amount added to the formulation can range from about 0.01 to 200% (w/w), preferably from approximately 1 to 50%, of the conjugate present. Such formulations may then lyophilized and milled to the desired particle size.

The properly sized particles may then suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants may include sorbitan trioleate and soya lecithin. Oleic acid may also be useful as a surfactant. This mixture may then loaded into the delivery device. An example of a commercially available metered dose inhaler suitable for use in the present invention is the Ventolin metered dose inhaler, manufactured by Glaxo Inc., Research Triangle Park, N.C.

Formulations for powder inhalers may comprise a finely divided dry powder containing conjugate and may also include a bulking agent, such as lactose, sorbitol, sucrose, or mannitol in amounts which facilitate dispersal of the powder from the device, e.g., 50% to 90% by weight of the formulation. The particles of the powder may have aerodynamic properties in the lung corresponding to particles with a density of about 1 g/cm.sup.2 having a median diameter less than 10 micrometers, preferably between 0.5 and 5 micrometers, most preferably of between 1.5 and 3.5 micrometers. An example of a powder inhaler suitable for use in accordance with the teachings herein is the Spinhaler powder inhaler, manufactured by Fisons Corp., Bedford, Mass. The powders for these devices may be generated and/or delivered by methods disclosed in U.S. Pat. No. 5,997,848, U.S. Pat. No. 5,993,783, U.S. Pat. No. 5,985,248, U.S. Pat. No. 5,976,574, U.S. Pat. No. 5,922,354, U.S. Pat. No. 5,785,049 and U.S. Pat. No. 5,654,007.

For oral preparations, the subject compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

The subject compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agent can also be delivered to the subject by enteral administration. Enteral routes of administration include, but are not necessarily limited to, oral and rectal (e.g., using a suppository) delivery.

Furthermore, the subject compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Dosages of the Compounds of the Invention

Depending on the subject and condition being treated and on the administration route, the subject compounds may be administered in dosages of, for example, 0.1 µg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is one which provides up to about 1 µg to about 1,000 µg or about 10,000 µg of subject composition to reduce a symptom in a subject animal.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound (s) in a composition as a solution in sterile water, normal saline or another pharmaceutically acceptable carrier.

Combination Therapy Using the Compounds of the Invention

For use in the subject methods, the subject compounds may be formulated with or otherwise administered in combination with other pharmaceutically active agents, including other CFTR-activating agents. The subject compounds may be used to provide an increase in the effectiveness of another chemical, such as a pharmaceutical (e.g., other CFTR-activating agents, or agents that affect cellular misprocessing of mutant-CFTR), or a decrease in the amount of another chemical, such as a pharmaceutical (e.g., other CFTR-activating agents), that is necessary to produce the desired biological effect.

Examples of other CFTR activating agents include, but are not limited to, enhancers of intracellular cAMP levels, such as for example, but not limited to, forskolin, rolipram, 8-bromo-cAMP, theophylline, papaverine, cAMP and salts, analogs, or derivatives thereof. Other examples include beta agonists, tobramycin (TOBIO, Chiron Inc., Emeryville, Calif.) and curcumin (Egan et al., (2004) Science 304:600-603).

The compounds described above may also be combined with other therapies for CF, including oral corticosteroids, ibuprofen, ribovarin or antibiotics such as dicloxacillin, cephalosporin, cephalexin, erythromycin, amoxicillin-clavulanate, ampicillin, tetracycline, trimethoprim-sulfamethoxazole, chloramphenicol ciprofloxacin, tobramycin, gentamicin, cephalosporins, monobactams and the like.

The compounds described herein for use in combination therapy with the compounds of the present invention may be administered by the same route of administration (e.g. intrapulmonary, oral, enteral, etc.) that the compounds are administered. In the alternative, the compounds for use in combination therapy with the compounds of the present invention may be administered by a different route of administration that the compounds are administered.

Kits

Kits with unit doses of the subject compounds, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Methods

Methods for Increasing Chloride Ion Permeability of a Mutant-CFTR Cell

The invention provides methods for increasing ion permeability of a cell that produces mutant-CFTR protein, with cells having a gating defective mutant-CFTR being of interest, with cells having a ΔF508-CFTR, G551D-CFTR, G1349D-CFTR, or D 152H-CFTR being of particular interest. In general, the method involves contacting the cell with a compound in an amount effective to activate the mutant-CFTR protein and increase ion permeability of the cell. In one embodiment of particular interest, a compound of the invention is used in the method in combination with a second mutant-CFTR activator or potentiator.

In many embodiments, the cell mutant-CFTR protein is present on the plasma membrane of the cell. Methods of detecting mutant-CFTR protein presence on the plasma membrane are well known in the art and can include but are not limited to, for example, labeling a molecule that binds to CFTR protein with a fluorescent, chemical or biological tag. Examples of molecules that bind to CFTR protein include, without limitation, antibodies (monoclonal and polyclonal), FAB fragments, humanized antibodies and chimeric antibodies. For an example of an antibody that binds to CFTR protein, see, e.g. U.S. Pat. No. 6,201,107.

In many embodiments, the cell has increased permeability to chloride ions, and the contacting of the cell with a compound of the invention, particularly when provided in combination with a mutant-CFTR activator or potentiator, increases the rate of chloride ion transport across the plasma membrane of the cell. Contacting the cell with a compound of the invention usually increases the activity of mutant-CFTR protein to increase ion transport.

In most embodiments, the ion transport activity of mutant-CFTR, or the permeability of a cell to ions, is increased by up to about 10%, by up to about 20%, by up to about 50%, by up to about 100%, by up to about 150%, by up to about 200%, by up to about 300%, by up to about 400%, by up to about 500%, by up to about 800%, or up to about 1000% or more. In certain embodiments, where there is no detectable ion transport activity of mutant-CFTR or permeability of a cell to ions, contacting of the cell with a compound of the invention causes detectable activity of mutant-CFTR or permeability of a cell to ions.

Activation of mutant-CFTR and/or ion permeability may be measured using any convenient methods that may use molecular markers, e.g., a halide sensitive GFP or another molecular marker (e.g., Galietta et al., (2001) *FEBS Lett.* 499, 220-224), patch clamp assays, and short circuit assays.

Suitable cells include those cells that have an endogenous or introduced mutant-CFTR gene. Suitable cells include mammalian cell systems (e.g., COS, CHO, BHK, 293, 3T3 cells etc.) harboring constructs that have an expression cassette for expression of mutant-CFTR. The cell used in the subject methods may be a cell present in vivo, ex vivo, or in vitro. As used herein, the term "expression cassette" is meant to denote a genetic sequence, e.g. DNA or RNA, that codes for mutant-CFTR protein, e.g., ΔF508-CFTR. Methods of introducing an expression cassette into a cell are well known in the art, see for example, Sambrook et al., *Molecular Cloning: A Laboratory Manual*. Cold Spring Harbor Laboratory Press, NY, Vol. 1, 2, 3 (1989).

Methods of Treating Cystic Fibrosis

The invention also provides methods of treating a subject having a condition associated with mutant-CFTR, e.g., cystic fibrosis. In general, the method involves administering to the subject a compound of the invention in an amount effective to activate a mutant-CFTR protein to increase ion transport and thereby treat the condition. In an embodiment of particular interest, a compound of the invention is administered in combination with a second mutant-CFTR activator or potentiator, e.g., a compound that enhances intracellular cAMP, e.g., forskolin.

The compounds disclosed herein are useful in the treatment of a mutant-CFTR-mediated condition, e.g., any condition, disorder or disease, or symptom of such condition, disorder, or disease, that results from the presence and/or activity of mutant-CFTR as compared to wild-type CFTR, e.g., activity of mutant-CFTR in ion transport. Such conditions, disorders, diseases, or symptoms thereof are amenable to treatment by activation of mutant-CFTR activity, e.g., activation of mutant-CFTR chloride transport. Cystic fibrosis, a hereditary condition associated with a mutant-CFTR, e.g., ΔF508-CFTR G551D-CFTR, G1349D-CFTR, or D1152H-CFTR, is an example of a condition that is treatable using the compounds of the invention. Use of the compounds of the invention in combination with a second mutant CFTR activator or potentiator is of particular interest.

Cystic fibrosis is predominantly a disorder of infants, children and young adults, in which there is widespread dysfunction of the exocrine glands, characterized by signs of chronic pulmonary disease (due to excess mucus production in the respiratory tract), pancreatic deficiency, abnormally high levels of electrolytes in the sweat and occasionally by biliary cirrhosis. Also associated with the disorder is an ineffective immunologic defense against bacteria in the lungs.

Pathologically, the pancreas shows obstruction of the pancreatic ducts by amorphous eosinophilic concretions, with consequent deficiency of pancreatic enzymes, resulting in steatorrhoea and azotorrhoea and intestinal malabsorption. The degree of involvement of organs and glandular systems may vary greatly, with consequent variations in the clinical picture.

Nearly all exocrine glands are affected in cystic fibroses in varying distribution and degree of severity. Involved glands are of three types: those that become obstructed by viscid or solid eosinophilic material in the lumen (pancreas, intestinal glands, intrahepatic bile ducts, gallbladder, submaxillary glands); those that are histologically abnormal and produce an excess of secretions (tracheobronchial and Brunner's glands); and those that are histologically normal but secrete excessive sodium and chloride (sweat, parotid, and small salivary glands). Duodenal secretions are viscid and contain an abnormal mucopolysaccharide. Infertility occurs in 98% of adult men secondary to maldevelopment of the vas deferens or to other forms of obstructive azoospermia. In women, fertility is decreased secondary to viscid cervical secretions, but many women with CF have carried pregnancies to term. However, the incidence of maternal complications increases.

Fifty percent of cystic fibrosis patients with pulmonary manifestations usually chronic cough and wheezing associated with recurrent or chronic pulmonary infections. Cough is the most troublesome complaint, often accompanied by sputum, gagging, vomiting, and disturbed sleep. Intercostal retractions, use of accessory muscles of respiration, a barrel-chest deformity, digital clubbing, and cyanosis occur with disease progression. Upper respiratory tract involvement includes nasal polyposis and chronic or recurrent sinusitis. Adolescents may have retarded growth, delayed onset of puberty, and a declining tolerance for exercise. Pulmonary complications in adolescents and adults include pneumothorax, hemoptysis, and right heart failure secondary to pulmonary hypertension.

Pancreatic insufficiency is clinically apparent in 85 to 90% of CF patients, usually presents early in life, and may be progressive. Manifestations include the frequent passage of bulky, foul-smelling, oily stools; abdominal protuberance; and poor growth pattern with decreased subcutaneous tissue and muscle mass despite a normal or voracious appetite. Rectal prolapse occurs in 20% of untreated infants and toddlers. Clinical manifestations may be related to deficiency of fat-soluble vitamins.

Excessive sweating in hot weather or with fever may lead to episodes of hypotonic dehydration and circulatory failure. In arid climates, infants may present with chronic metabolic alkalosis. Salt crystal formation and a salty taste on the skin are highly suggestive of CF.

Insulin-dependent diabetes develops in 10% of adult patients having CF, and multilobular biliary cirrhosis with varices and portal hypertension develops in 4 to 5% of adolescents and adults. Chronic and/or recurrent abdominal pain may be related to intussusception, peptic ulcer disease, periappendiceal abscess, pancreatitis, gastroesophageal reflux, esophagitis, gallbladder disease, or episodes of partial intestinal obstruction secondary to abnormally viscid fecal contents. Inflammatory complications may include vasculitis and arthritis.

Any of above symptoms of CF may be treated using the compounds of the invention, with use of such compounds in combination with a second mutant-CFTR activator or potentiator being of particular interest.

The above methods may be used to treat CF and its symptoms in humans or in animals. Several animal models for CF are known in the art. For example, Engelhardt et al. (*J. Clin. Invest.* 90: 2598-2607, 1992) developed an animal model of the human airway, using bronchial xenografts engrafted on rat tracheas and implanted into nude mice. More recently transgenic models of cystic fibrosis have been produced (e.g., Clarke et al., *Science* 257: 1125-1128, 1992; Dorin et al., *Nature* 359: 211-215, 1992). With the recent advances of nuclear transfer and stem cell transformation technologies, the alteration of a wild type CFTR gene in an animal to make it into a mutant-CFTR gene is possible for a wide variety of animals.

Many of these animals show human CF symptoms. In particular, many of these animals showed measurable defects in ion permeability of airway and intestinal epithelia, similar to those demonstrable in human CF tissues, and a susceptibility to bacterial infection. Furthermore, most of the deficient mice had intestinal pathology similar to that of meconium ileus. Also, there appeared to be no prenatal loss from litters produced from crosses between heterozygotes.

Animals suitable for treatment using the subject methods include any animal with a mutant-CFTR related condition, particularly a mammal, e.g., non-human primates (e.g., monkey, chimpanzee, gorilla, and the like), rodents (e.g., rats, mice, gerbils, hamsters, ferrets, and the like), lagomorphs, swine (e.g., pig, miniature pig), equine, canine, feline, and the like. Large animals are of particular interest. Transgenic mammals may also be used, e.g. mammals that have a chimeric gene sequence. Methods of making transgenic animals are well known in the art, see, for example, U.S. Pat. No. 5,614,396. For an example of a transgenic mouse with a CFTR defect, see e.g. WO 94/04669.

Such animals may be tested in order to assay the activity and efficacy of the subject compounds. Improvement in lung function can be assessed by, for example, monitoring prior to and during therapy the subject's forced vital capacity (FVC), carbon monoxide diffusing capacity ($DL_{CO}$), and/or room air $pO_2$>55 mmHg at rest. Significant improvements in one or more of these parameters are indicative of efficacy. It is well within the skill of the ordinary healthcare worker (e.g., clinician) provide adjust dosage regimen and dose amounts to provide for optimal benefit to the patient according to a variety of factors (e.g., patient-dependent factors such as the severity of the disease and the like), the compound administered, and the like).

Subjects Suitable for Treatment

Subjects suitable for treatment with a method of the present invention include individuals having mutant-CFTR protein-mediated condition disorder or disease, or symptom of such condition, disorder, or disease that results from or is correlated to the presence of a mutant-CFTR, usually two alleles of the mutant CFTR. Moreover, subjects suitable for treatment with a method of the present invention include individuals with Cystic Fibrosis (CF). Of particular interest in many embodiments is the treatment of humans with CF.

Symptoms of mutant-CFTR protein-mediated conditions include meconium ileus, liver disease including biliary tract obstruction and stenosis, pancreatic insufficiency, pulmonary disease including chronic *Pseudomonas aeruginosa* infections and other infections of the lung, infertility associated with abnormal vas deferens development or abnormal cervical mucus, and carcinoma including adenocarcinoma.

The compounds of the present invention affect the ion transport capability of the mutant-CFTR by increasing the reduced level of ion transport mediated by a mutant-CFTR, such as the ΔF508-CFTR, G551D-CFTR, G1349D-CFTR, or D1152H-CFTR. As such, the compounds of the present invention have particular clinical utility in treating a subset of CF patients that have mutations in the CFTR gene that results a mutant-CFTR that is expressed in the plasma membrane and has reduced chloride conductance capability or has abnormal regulation of conductance (i.e., the mutant-CFTR is gating defective). As such, the compounds of the present invention have clinical utility in treating CF patients having a gating-defective mutant-CFTR, such as ΔF508-CFTR, G551D-CFTR, G1349D-CFTR, or D1152H-CFTR. In addition, the compounds of the present invention also have clinical utility in treating CF patients when used in conjunction with compounds that correct cellular misprocessing of a mutant-CFTR, such as ΔF508-CFTR.

CFTR mutations associated with CF are well known in the art. These mutations can be classified in five general categories with respect to the CFTR protein. These classes of CFTR dysfunction include limitations in CFTR production (e.g., transcription and/or translation) (Class I), aberrant folding and/or trafficking (Class II), abnormal regulation of conduction (Class III), decreases in chloride conduction (Class IV), and reductions in synthesis (Class V). Due to the lack of functional CFTR, Class I, II, and III mutations are typically associated with a more severe phenotype in CF (i.e. pancreatic insufficiency) than the Class IV or V mutations, which may have very low levels of functional CFTR expression. A listing of the different mutations that have been identified in the CFTR gene is as found at the world-wide website of the Cystic Fibrosis Mutation Database at genet.sickkids.on.ca/cgi-bin/WebObjects/MUTATION, specifically incorporated by reference herein in its entirety.

A subject suitable for treatment with a method of the present invention may be homozygous for a specific mutant-CFTR, i.e. homozygous subjects with two copies of a specific mutant-CFTR, e.g., ΔF508-CFTR. In addition, subjects suitable for treatment with a method of the present invention may also be compound heterozygous for two different CFTR mutants, i.e., wherein the genome of the subjects includes two different mutant forms of CFTR, e.g., a subject with one copy of ΔF508-CFTR and a copy of different mutant form of CFTR.

In some embodiments of the invention, the mutant-CFTR polypeptide is ΔF508-CFTR. In other embodiments of the invention, the mutant-CFTR polypeptide is G551 D-CFTR. In yet other embodiments of the invention, the mutant-CFTR polypeptide is G1349D-CFTR. In still other embodiments of the invention, the mutant-CFTR polypeptide is D152H-CFTR. The invention, however, should not be construed to be limited solely to the treatment of CF patients having this mutant form of CFTR. Rather, the invention should be construed to include the treatment of CF patients having other mutant forms of CFTR with similar characteristics, that result in expression of the mutant-CFTR in the plasma membrane and has reduced chloride conductance capability or has abnormal regulation of conductance.

Rational Therapy

The invention also provides rational therapy-based methods for treating a subject having a condition associated with a mutant-CFTR, e.g., cystic fibrosis. In general, the method involves determining the underlying CFTR mutation of the patient and selecting a treatment regimen for administering to the patient based on the CFTR mutation, where the compound selected for administration is one having activity that provides for improved function of the particular CFTR mutant. Of particular interest is administration of a compound having enhanced activity for the particular CFTR mutant of the patient compared to other compounds of the same genus or class. In this manner, the clinician can more readily prescribe a successful therapy, based on selection of a compound in light of the CFTR mutation in the patient. Therefore, the selected treatment regimen is more effective and rationally based. Moreover, such rational therapy can significantly reduce therapy-associated toxicity.

As used herein, the process of determining the CFTR mutation of a patient includes any suitable method, of which many are known in the art. Suitable methods include determining the DNA sequence, or by detecting an RNA transcript corresponding to such DNA sequence, of a polymorphic gene. Various other detection techniques suitable for use in the present methods will be apparent to those conversant with methods of detecting, identifying, and/or distinguishing CFTR mutations. Such detection techniques include but are not limited to direct sequencing, use of "molecular beacons" (oligonucleotide probes that fluoresce upon hybridization, useful in real-time fluorescence PCR; see e.g., Marras et al., Genet Anal 14:151 (1999)); electrochemical detection (reduction or oxidation of DNA bases or sugars; see U.S. Pat. No. 5,871,918 to Thorp et al.); rolling circle amplification (see, e.g., Gusev et al., Am J Pathol 159:63 (2001)); Third Wave Technologies (Madison Wis.) INVADER non-PCR based detection method (see, e.g., Lieder, Advance for Laboratory Managers, 70 (2000)).

Accordingly, any suitable detection technique as is known in the art may be utilized in the present methods to genotype the subject. Furthermore, suitable biological specimens to use for determining the CFTR mutation of the subject are those which comprise cells and DNA and include, but are not limited to blood or blood components, dried blood spots, urine, buccal swabs and saliva.

In practicing the subject methods, once the underlying CFTR mutation of the patient is determined, it is used to select a compound that will be most effective for the underlying CFTR mutation. For example, where the subject has ΔF508-CFTR mutation, the patient will be administered will be administered a composition containing a sulfonamide containing compound in either a mono-drug therapy or in combination with another compound as described above. Where the subject has a non ΔF508-CFTR mutation, the patient will be treated with phenylglycine-containing compound in either a mono-drug therapy or in combination with another compound as described above. For example, where the subject has a gating defective CFTR mutation, such as a class III mutation (e.g., G551D-CFTR, G1349D-CFTR, or D1152-CFTR), the subject is treated with a phenylglycine containing compound in either a mono-drug therapy or in combination with another compound as described above.

In certain embodiments, once the underlying CFTR mutation of the patient is determined, in silico modeling of the mutant-CFTR performed and 3D models of the subject compounds are screened in order to select a compound having enhanced activity for the particular CFTR mutant of the patient compared to other compounds of the same genus or class. An exemplary in silico modeling program suitable for use with the subject method is the PREDICT™ 3D Modeling Technology (Predix Pharmaceuticals, Woburn Mass.), described in greater detail in Becker et al., PNAS 101(31): 11304-11309 (2004).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The following methods and materials are used in the examples below.

Cell Lines

Clonal populations of Fischer rat thyroid (FRT) epithelial cells stably co-expressing human ΔF508-CFTR and the high-sensitivity halide-sensing green fluorescent analog YFP-H148Q/I152L (Galietta et al., A.S. (2001) FEBS Lett. 499, 220-224) were generated by liposome transfection and limiting dilution with Zeocin/G418 selection. More than 100 clones were evaluated for high fluorescence and ΔF508-CFTR plasma membrane targeting after growth at 27° C. for 24 hours. For screening, cells were cultured on plastic in Coon's modified F12 medium supplemented with 10% fetal bovine serum, 2 mM L-glutamine, 100 U/ml penicillin, and 100 μg/ml streptomycin, and plated on black 96-well microplates (Corning-Costar 3904) at 30,000 cells/well. For short-circuit measurements cells were cultured on Snapwell permeable supports (Corning-Costar) at 500,000 cells/insert. Human nasal epithelium cells from CF patients were cultured on Snapwell inserts and allowed to differentiate in a hormone-supplemented medium (Galietta et al., Am. J. Physiol., 275:19723-19728 (1998)). Some measurements were done using stably transfected FRT cells expressing YFP-H148Q and wildtype- or G551D-CFTR (Galietta et al., (2001) J. Biol. Chem. 276, 19723-19728). Patch clamp experiments were done on ΔF508-CFTR-expressing FRT cells plated in 35-mm Petri dishes.

Compounds

A collection of 50,000 diverse drug-like compounds (purchased from ChemBridge Co.) was used for initial screening. For optimization, compounds identified in the primary screen were purchased from ChemDiv (out of 600,000 available compounds). Compounds were prepared as 10 mM stock solutions in DMSO. Secondary plates containing one or four compounds per well were prepared for screening (0.25 mM in DMSO). Compounds for secondary analysis were resynthesized, purified, and confirmed by NMR and liquid choromatography/mass spectrometry.

Screening Procedures

Screening was carried out using a Beckman integrated system containing a 3-meter robotic arm, $CO_2$ incubator containing microplate carousel, plate-washer, liquid handling workstation, bar code reader, delidding station, plate sealer, and two FluoStar fluorescence plate readers (Galaxy, BMG Lab Technologies), each equipped with dual syringe pumps and HQ500/20X (500±10 μm) excitation and HQ535/30M (535±15 nm) emission filters (Chroma). Software was written in VBA (Visual Basic for Applications) to compute baseline-subtracted fluorescence slopes (giving halide influx rates).

For assay of ΔF508-CFTR potentiator activity the incubator (27° C., 90% humidity, 5% $CO_2$/95% air) was loaded with forty-to-sixty 96-well plates containing FRT cells. After an 18-24 hour incubation plates were washed 3 times with PBS (300 μl/wash) leaving 50 μl PBS. 10 μl of PBS containing 120 μM forskolin was added, and after 5 min test compounds (0.6 μl of 0.25 mM DMSO solution) were added to each well to give 2.5 μM final compound concentrations. After 15 min, 96-well plates were transferred to a plate reader for fluorescence assay. Each well was assayed individually for $I^-$ influx by recording fluorescence continuously (200 ms per point) for 2 seconds (baseline) and then for 12 seconds after rapid (<1 s) addition of 160 μL of isosmolar PBS in which 137 mM $Cl^-$ was replaced by $I^-$. $I^-$ influx rates were computed from initial fluorescence versus time-curve slopes (determined by $3^{rd}$ order polynomial regression) after normalization for total fluorescence (background subtracted initial fluorescence). All compound plates contained negative control (DMSO vehicle alone) and positive controls (genistein, 5 μM and 50 μM). Assay analysis indicated a Z'-factor of >0.7 (Zhang et al., J. Biomol. Screen 4:67-73 (1999)).

Whole-Cell Patch-Clamp

Experiments were performed in the cell-attached configuration of the patch-clamp technique on FRT cells expressing ΔF508-CFTR. Cells were seeded at a density of $10^4$ cells/well and grown at 37° C. for 24-48 hours and then incubated for 24-48 hours at 27° C. to allow trafficking of the ΔF508 protein to the plasma membrane. Borosilicate glass pipettes were fire polished to obtain tip resistances of 2-4 MΩ. Currents were sampled at 500 Hz using a patch-clamp amplifier (EPC-7, List, Darmstadt) and low-pass filtered using a 4-pole Bessel filter set at a cutoff frequency of 250 Hz and digitized at 500 Hz using an ITC-16 data translation interface (Instrutech). The extracellular (bath) solution contained (in mM): 150 NaCl, 1 $CaCl_2$, 1 $MgCl_2$, 10 glucose, 10 mannitol, and 10 TES (pH 7.4). The pipette solution contained (in mM): 120 CsCl, 1 $MgCl_2$, 10 TEA-Cl, 0.5 EGTA, 1 Mg-ATP, and 10 Hepes (pH 7.3). Membrane conductances were monitored by alternating the membrane potential between +80 and −100 mV. Current-voltage relationships were generated by applying voltage pulses between −100 and +100 mV in 20 mV steps. Analysis of open channel probability ($P_o$), mean channel open time ($T_o$), and mean channel closed time ($T_c$) was done using recordings of at least three minute intervals (Taddei et al., FEBS Lett. 558:52-56 (2004)).

Short-Circuit Current Measurements

Using chamber experiments were performed 7-9 days after plating ΔF508-CFTR expressing FRT cells on Snapwell inserts. The basolateral solution contained (in mM): 130 NaCl, 2.7 KCl, 1.5 $KH_2PO_4$, 1 $CaCl_2$, 0.5 $MgCl_2$, 10 glucose, 10 Na-Hepes (pH 7.3). In the apical bathing solution 65 mM NaCl was replaced by Na gluconate, and $CaCl_2$ was increased to 2 mM. Solutions were bubbled with air and maintained at 37° C. The basolateral membrane was permeabilized with 250 μg/ml amphotericin B. The hemichambers were connected to a DVC-1000 voltage clamp (World Precision Instruments) via Ag/AgCl electrodes and 1 M KCl agar bridges for recording short-circuit current.

Synthetic Chemistry $^1$H spectra were obtained in $CDCl_3$ or $d_6$-DMSO using a Mercury 400 MHz spectrometer. Flash column chromatography was done using EM silica gel (230-400 mesh). Thin layer chromatography was carried out on Merk silica gel 60 F254 plates and visualized under a UV lamp. Microwave reactions were carried out on an Emrys synthesizer. Representative synthetic schemes for a phenylglycine and sulfonamide follow (FIG. 2, panel B).

For synthesis of compound P-1, to a solution of N-tert-butoxycarbonyl-N-methylphenylgycine (compound I) (1.26 g, 4.75 mmol) at room temperature was added p-isopropylaniline (705 mg, 5.22 mmol), 4-(N,N-dimethylamino) pyridine (DMAP) (116 mg, 0.92 mmol) in $CH_2Cl_2$ (25 mL), and 1-ethyl-3-[3-(dimethylamino)-propyl]carbodiimide (EDCI, 1.00 g, 5.22 mmol). The reaction mixture was stirred for 2 hours and then quenched by pouring over saturated $NH_4Cl$. After extraction with $CH_2Cl_2$ the organic layer was washed successively with water and brine, dried ($Na_2SO_4$), and concentrated in vacuo. Column chromatography of the crude residue gave [(4-isopropylphenylcarbamoyl)-phenylmethyl]-methylcarbamic acid tert-butyl ester (compound IIA) as a white solid (1.67 g, 92%). Compound IIA (300 mg, 0.785 mmol) was dissolved in a minimal quantity of trifluoroacetic acid (TFA), maintained at room temperature for 15 min, poured over aqueous $NaHCO_3$, and extracted with $CH_2Cl_2$. Washing, drying and evaporation of the organic layer gave compound II as a yellow oil (218 mg, 98%). To a mixture of compound II (177 mg, 0.620 mmol), indole-3-acetic acid (114 mg, 0.651 mmol) and DMAP (15 mg, 0.124 mmol) in $CH_2Cl_2$ (5 mL), EDCI (131 mg, 0.682 mmol) was added at room temperature. The reaction mixture was worked up as for compound IIA and recrystallized from $CH_2Cl_2$:

MeOH (9:1) to give compound P-1 as a white solid (1.67 g, 92%). Mass (ES$^+$): M/Z=440 [M+1]$^+$; $^1$H NMR δ 1.21 (d, $^6$H, J=6.9 Hz), 2.85 (sep, $^1$H, J=6.9 Hz), 2.95 (s, $^3$H), 3.91 (s, $^2$H), 6.55 (s, $^1$H), 7.08-7.40 (m, 13H), 7.59 (d, $^1$H, J=7.8 Hz), 7.88 (bs, $^1$H), 8.13 (bs, $^1$H).

For synthesis of compound S-3, compound III (Blus, Dyes and Pigments 41:149-157 (1999)) (2.21 g, 8.0 mmol) and diethylethoxymethylenemalonate (1.81 g, 8.4 mmol) were dissolved in tetrahydrofuran (THF) (4 mL), and the solution was heated to 140° C. for 30 min until the THF and ethanol by-product evaporated. The residue was diluted with ethyl acetate (EtOAc), washed with brine, dried with $Na_2SO_4$, and evaporated to dryness. Flash chromatography gave light yellow solid compound IIIB (3.29 g, 90%). To a solution of phenyl ether ($Ph_2O$, 3 mL) and compound IIIB (130 mg, 0.30 mmol) in an Emrys microwave reaction vessel was added 4-chlorobenzoic acid (1 mg, 0.02 mmol). The solution was microwave irradiated at 250° C. for 75 min. The white precipitate was filtered and washed with hexane to yield compound IV (48 mg, 42%). To an Emrys microwave reaction vessel (0.2-0.5 mL) containing compound IV (65 mg, 0.083 mmol) was added o-methoxybenzyl amine (200 mg, 1.4 mmol) and microwave irradiated at 180° C. for 30 min. The resulting solution was diluted with dichloromethane and water, and extracted with EtOAc three times. After washing, drying and evaporation, the residue was purified by flash chromatography giving compound S-3 as a white powder (27 mg, 35%). Mass (ES+): M/Z=492 [M+1]$^+$; $^1$H NMR $CDCl_3$ δ 1.08 (t, 3H, J=7.2 Hz), 3.65 (q, $^2$H, J=7.2 Hz), 3.79 (s, $^3$H), 4.70 (d, 2H, J=6.0 Hz), 6.81 (m, 2H), 7.02 (m, $^2$H), 7.16 (td, $^1$H, J=8.0, 1.6 Hz), 7.23 (d, $^1$H, J=7.2 Hz), 7.29 (m, 2H), 7.37 (d, $^1$H, J=8.4 Hz), 7.53 (dd, $^1$H, J=8.8, 2.0 Hz), 8.77 (d, $^1$H, J=2.0 Hz), 8.83 (d, $^1$H, J=6.4 Hz), 10.74 (t, $^1$H, J=5.6 Hz), 12.30 (d, $^1$H, J=4.4 Hz).

Assay of cAMP cAMP activity was measured using the BIOTRAK enzymatic immunoassay (Amersham) of FRT cell lysates after incubation with the compounds for 10 minutes in the presence of 0.5 μM forskolin.

Pharmacokinetics

To increase compound solubility, potentiators were dissolved in a liposomal formulation containing 5 mg potentiator in 21.3 mg hydrogenated soy phosphatidylcholine, 5.2 mg cholesterol, 8.4 mg distearoylphosphatidylglycerol, and 90 mg sucrose in 5 ml PBS. A bolus of potentiator-containing solution (5 mg/kg) was administered intravenously in rats over 1 min (male Sprague-Dawley rats, 360-420 grams) by a jugular vein catheter. Arterial blood samples (1 ml) were obtained at predetermined times for LCMS analysis.

Liquid Chromatography/Mass Spectrometry (LCMS)

For analysis of blood samples, collected plasma was chilled on ice, and ice-cold acetonitrile (2:1 v:v) was added to precipitate proteins. Samples were centrifuged at 4° C. at 20,000 g for 10 min. Supernatants (supplemented with sulforhodamine 101 as internal standard) were analyzed for compound P-1 and compound S-3 by extraction with C-18 reversed-phase cartridges (1 ml, Alltech Associates, Inc. Deerfield, Ill.) by standard procedures. The eluate was evaporated, and the residue was reconstituted in 100 μl of mobile phase for HPLC analysis. Reversed-phase HPLC separations were carried out using a Supelco C18 column (2.1×100 mm, 3 μm particle size) connected to a solvent delivery system (Waters model 2690, Milford, Mass.). The solvent system consisted of a linear gradient from 20% $CH_3CN$/10 mM $KH_2PO_4$, pH 3 to 95% $CH_3CN$/10 mM $KH_2PO_4$, pH 3 over 10 min, followed by 6 min at 95% $CH_3CN$/20 mM $NH_4OAc$ (0.2 ml/min flow rate). Compounds P-1 and S-3 were detected at 256 nm, after establishing a linear standard calibration curve in the range of 20-5000 nM. The detection limit was 10 nM and recovery was >90%. Mass spectra were acquired on a mass spectrometer (Alliance HT 2790+ZQ) using negative ion detection, scanning from 200 to 800 Da (Sonawane et al., J. Pharm. Sci. 94:134-143 (2004)).

Stability in Hepatic Microsomes

Compounds P-1 and S-3 (10 μM each) were incubated separately with a phosphate buffered (100 mM) solution of rat liver microsomes (2 mg protein/ml, Sigma) containing NADPH (0 or 1 mM) for 60 min at 37° C. After 60 min the mixture was chilled on ice, and 0.5 ml of ice-cold acetonitrile was added to precipitate the proteins for LCMS analysis as described above.

Example 1

Screening Assays and Structure-Activity Relationship

The high-throughput screen was designed to identify compounds that activated ΔF508-CFTR when expressed at the cell plasma membrane. FRT epithelial cells co-expressing ΔF508-CFTR and a high sensitivity yellow fluorescent protein-based halide indicator were incubated at 27° C. for 24 h to permit ΔF508-CFTR plasma membrane targeting (FIG. 1, panel A). After washing, forskolin (20 μM) and test compounds (2.5 μM) were added to individual wells of 96-well plates. The I⁻ influx assay was carried out ~15 min later by measurement of the time course of decreasing YFP fluorescence after creation of an inwardly-directed I⁻ gradient. A high concentration of forskolin was used to identify ΔF508-CFTR potentiators that may interact directly with ΔF508-CFTR rather than alter cAMP concentration. Since activation of CFTR requires cAMP stimulation, forskolin, an enhancer of cAMP, was added to the in vitro models in order to mimic the cellular cAMP stimulation. Each plate also contained positive control wells in which a dose-response was done for genistein, a known (though low potency) ΔF508-CFTR potentiator. The screening revealed many compounds that at 2.5 μM increased I⁻ influx as much as the reference compound genistein at 50 μM, and substantially greater than forskolin (20 μM) alone (see FIG. 1, panel B). FIG. 2, panel A, depicts representative structures of the two classes of compounds identified by the subject screen.

The strong potentiators were subjected to secondary analysis to select a subset for further analysis. More than 300 structural analogs were evaluated to establish structure-activity relationships and to identify compounds with improved potency. Dose-response studies were done to determine $K_a$ and $V_{max}$, with representative data shown in FIG. 3, panel A (phenylglycine containing compounds) and panel B (sulfonamide containing compounds). Dose response data from the fluorescence assay for the most active compounds of each class is shown in FIG. 3, panel C, with data for comparison shown for genistein and the tetrahydrobenzothiophene ΔF508$_{act}$-02. Many compounds were identified that activated ΔF508-CFTR chloride conductance by 50% at concentrations under 1 μM. Several of these compounds are shown in Tables 1, along with data as to the activity of these compounds as ΔF508-CFTR potentiators. By short-circuit current analysis, the most potent compounds activated ΔF508-CFTR chloride strongly at concentrations well under 100 nM. The maximal current was similar to that of tetrahdrobenzothiophene and flavone-type compounds.

The results of the structure-activity relationship are summarized Table 1 and Table 2, and the principle conclusions of the structure-activity relationship are provided in FIG. 2, panel C. Active phenylglycine containing compounds contained a disubstituted glycyl amine with amide of aromatic amines. Substitutions at $R_1$ had relatively little effect on compound activity. Most active compounds had as $R_1$ 4-isopropylphenyl, with reduced activity for $R_1$ as benzo[3,4-b][1,4]dioxane in (P-2, P-4) or 4-methoxyphenyl (P-5). Evaluation of $R_2$ substitutions indicated that replacement of hydrogen by methyl (PG-07) or methoxy (PG10) strongly reduced potency. The R2 phenyl group appeared to be important for activity as its replacement by indol-3-methyl reduced activity. All potent compounds had as R3 a methyl, as its replacement by hydrogen (PG-06) or furfuryl-2-methyl reduced activity. Most active compounds had as R4 an indolyl-3-acetyl, as substitution by thiophene-2-acetyl or diphenyl acetyl resulted in loss of activity. Thus, greatest ΔF508-CFTR activating potency was produced by hydrophobic R1, R2, and R3, with R4 as indolyl-2 (or 3)-acetyl.

The results of the structure-activity relationship analysis of sulfonamides show that the requirement of 3-carboxamide and 6-aminosulfo groups. All quinolone compounds had as $R_1$ hydrophobic groups such as alkoxy, dialkyl, alkyl, and halo substituted phenyl or cyclohexyl groups (S-1). Greatest activity was found for $R_2$ as non-polar alkyl chains (ethyl, methyl, 2-propenyl). The most potent compounds (S-2, S-3, and S-4) contained an ethyl group at $R_2$ in combination with phenyl as $R_1$, and linear alkyl group as $R_3$. Substitutions at $R_3$ with non-polar linear or branched alkyl or cycloalkyl groups improved activity. In general, greatest potency was found with hydrophobic-nonpolar substitutions on sulfonamide and carboxamide moieties

TABLE 1

Structure-activity relationship analysis of phenylglycine containing compounds

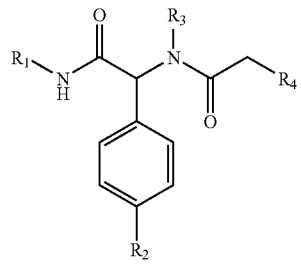

| Compd | R1 | R2 | R3 | R4 | Ka (μM) |
|---|---|---|---|---|---|
| P-1 | 4-Isopropyl-Ph | H | Me | Indol-3-actyl | 0.30 |
| P-2 | 2,3-diH-1,4-benzodioxin-6-yl | H | Me | Ac-NHCH₂CO— | 0.30 |
| P-3 | 4-Isopropyl-Ph | 4-OMe | Me | Indol-3-actyl | 0.34 |
| P-4 | 2,3-diH-1,4-benzodioxin-6-yl | H | Me | Indol-3-acetyl | 0.40 |
| P-5 | 4-OMe-Ph | H | Me | Indol-3-acetyl | 0.70 |
| P-6 | 4-Isopropyl-Ph | H | H | Indol-3-acetyl | 0.88 |
| P-7 | 1,3-benzodioxol-5-yl | 4-Me | Me | Indol-3-acetyl | 1.33 |

TABLE 1-continued

Structure-activity relationship analysis of phenylglycine containing compounds

| Compd | R1 | R2 | R3 | R4 | Ka (µM) |
|---|---|---|---|---|---|
| P-8 | 4-OMe-Ph | 4-OMe | Me | Indol-3-acetyl | 2.13 |
| P-9 | 2,3-diH-1,4-benzodioxin-6-yl | 4-Me | H | Indol-2-acetyl | 2.33 |
| P-10 | 2,3-diH-1,4-benzodioxin-6-yl | 4-OMe | Me | Indol-3-acetyl | 2.71 |
| P-11 | 4-Isopropyl-Ph | 4-Me | 2-Furanylmethyl | Indol-3-acetyl | Moderate Activity |
| P-12 | 4-OMe-Ph | 4-Me | Me | Indol-3-acetyl | |
| P-13 | 4-OMe-Ph | 4-Me | 2-Furanylmethyl | Indol-3-acetyl | |
| P-14 | 4-OMe-Ph | 4-OMe | 2-Furanylmethyl | Indol-3-acetyl | |
| P-15 | 3-Me-Ph | Indol-3-$CH_2$—* | H | 2,2-Di-Ph-acetyl | |
| P-16 | 3,4-Di-Me-Ph | Indol-3-$CH_2$—* | H | 2,2-Di-Ph-acetyl | |

*-Ph-R2 group is replaced by indol-3-$CH_2$— group

TABLE 2

Structure-activity relationship analysis of sulfonamide containing compounds

| Compd | R1 | R2 | R3 | Ka uM) |
|---|---|---|---|---|
| S-1 | 2-OEt-Ph | Me | 2-propenyl | 0.30 |
| S-2 | Ph | Et | Cycloheptyl | 0.02 |
| S-3 | Ph | Et | 2-OMe-Ph-$CH_2$ | 0.03 |
| S-4 | Ph | Et | Cyclohexyl | 0.03 |
| S-5 | OEt-Ph | Me | n-Pentyl | 0.06 |
| S-6 | Ph | 2-propenyl | n-butyl | 0.11 |
| S-7 | Ph | 2-propenyl | Cycloheptyl | 0.12 |
| S-8 | 2,5-Di-Me-Ph | Me | 2-Pyridinylmethyl | 0.13 |
| S-9 | Ph | Et | (3-OMe)-propyl | 0.14 |
| S-10 | —$CH_2$—$CH_2$—CH(Me)—$CH_2$—$CH_2$— | H | 3[(N-(n-butyl)phenylamino)propyl | 0.14 |
| S-11 | Ph | 2-propenyl | 2-Pyridinylmethyl | 0.16 |
| S-12 | Ph | 2-Propenyl | n-Hexyl | 0.19 |
| S-13 | 2-Me-Ph | Me | n-butyl | 0.20 |
| S-14 | 2-EtO-Ph | Me | (Tetrahydro-2-furanyl)methyl | 0.20 |
| S-15 | 3-Me-Ph | Me | n-pentyl | 0.22 |
| S-16 | Ph | Et | 2-(1-cyclohexen-1-yl)ethyl | 0.24 |
| S-17 | Ph | Et | (Tetrahydro-2-furanyl)methyl | 0.24 |
| S-18 | 2-Et-Ph | Me | 2-Pyridinylmethyl | 0.27 |
| S-19 | 2,5-Di-Me-Ph | Me | 3-OMe-propyl | 0.29 |
| S-20 | 2,6-Di-Me-Ph | Me | n-Butyl | 0.33 |
| S-21 | 4-F-Ph | Et | Cyclopentyl | 0.33 |
| S-22 | 4-Et-Ph | Me | 2-(Di-OEt)ethyl | 0.36 |
| S-23 | 2-OMe-5-Cl-Ph | Me | 2(1-Cyclohexene-1-yl)ethyl | 0.37 |
| S-24 | Et | Et | 1,3-Benzodioxol-5-lymethyl | 0.38 |
| S-25 | 3-Me-Ph | Me | 1-Me-propyl | 0.44 |
| S-26 | 2-Et-Ph | Me | 1-Me-Propyl | 0.44 |

TABLE 2-continued

Structure-activity relationship analysis of sulfonamide containing compounds

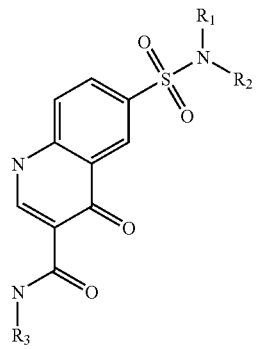

| Compd | R1 | R2 | R3 | Ka uM) |
|---|---|---|---|---|
| S-27 | Ph | Et | 2-Furanylmethyl | 0.46 |
| S-28 | 3-Me-Ph | Et | 3-OMe-Propyl | 0.48 |
| S-29 | 3-Me-Ph | Me | 2(1-cyclohexene-1-yl)ethyl | 0.49 |
| S-30 | 4-F-Ph | Et | (Tetrahydro-2-furanyl)methyl | 0.54 |
| S-31 | 3-Me-Ph | Me | n-Propyl | 0.56 |
| S-32 | -(2-Benzo-CH$_2$—CH$_2$)— ** | H | Cyclohexyl | 0.57 |
| S-33 | Ph | Et | 4-Me-Ph-CH$_2$— | 0.59 |
| S-34 | Cyclohexyl | Me | (Diethoxycarbonyl)methyl | 0.59 |
| S-35 | 3-Me-Ph | Et | 2-OMe-Ph-CH$_2$— | 0.60 |
| S-36 | 2-Et-Ph | Me | 3-OEt-propyl | 0.62 |
| S-37 | Ph | 2-Propenyl | 2-Furanylmethyl | 0.65 |
| S-38 | 4-Cl-2-F-Ph | Me | (Tetrahydro-2-furanyl)methyl | 0.66 |
| S-39 | Et | Et | 4-OMe-Ph-CH$_2$— | 0.66 |
| S-40 | 3-Me-Ph | Et | 3-Me-n-Butyl | 0.72 |
| S-41 | Et | Et | n-Butyl | 0.74 |
| S-42 | -(2-Benzo-CH$_2$—CH$_2$)— ** | H | 3-Me-butyl | 0.76 |
| S-43 | 2-Et-Ph | Me | (2-OMe)-ethyl | 0.77 |
| S-44 | —CH$_2$—CH$_2$—C(OCH$_2$—CH$_2$—O)CH$_2$—CH$_2$— | H | (2-OMe-Ph)methyl | 0.80 |
| S-45 | 4-Br-Ph | Me | (1-Me)propyl | 0.81 |
| S-46 | 3,4-Di-Me-Ph | Me | Propyl | 0.84 |
| S-47 | 2-Me-Ph | Me | 3-Me-Butyl | 0.87 |
| S-48 | —CH$_2$—CH$_2$—C(OCH$_2$—CH$_2$—O)CH$_2$—CH$_2$— | H | n-Pentyl | 0.88 |
| S-49 | —CH$_2$—CH$_2$—CH(Me)—CH$_2$—CH$_2$— | H | n-Pentyl | 0.88 |
| S-50 | 4-F-Ph | Et | 3-OMe-Propyl | 1.02 |
| S-51 | 3-Me-Ph | Et | (Tetrahydro-2-furanyl)methyl | 1.11 |
| S-52 | 2-Et-Ph | Me | 2-Propenyl | 1.14 |
| S-53 | Ph | Et | Isopropyl | 1.16 |
| S-54 | 2-OEt-Ph | Me | n-Octanyl | 1.16 |
| S-55 | 4-F-Ph | Me | Propyl | 1.25 |
| S-56 | —CH$_2$—CH(Me)—CH$_2$—CH$_2$—CH$_2$— | H | n-Butyl | 1.27 |
| S-57 | Ph | Et | n-Hexyl | 1.28 |
| S-58 | 2-Et-Ph | Me | 2-(Di-OEt)ethyl | 1.28 |
| S-59 | 2-Me-Ph | Me | 1-Me-Propyl | 1.28 |
| S-60 | 2-F-4-Cl-Ph | Me | (3-OEt)-n-Propyl | 1.37 |
| S-61 | 2,6-Di-Me-Ph | Me | (3-OMe)-n-Propyl | 1.42 |
| S-62 | 2-F-4-Cl-Ph | Me | n-Propyl | 1.45 |
| S-63 | —CH$_2$—CH$_2$—CH(Me)—CH$_2$—CH$_2$— | H | n-Hexyl | 1.53 |
| S-64 | 4-F-Ph | Et | n-Butyl | 1.56 |
| S-65 | 2-Me-Ph | Me | 3-OEt-Propyl | 1.66 |

Example 2

Short-Circuit Current Analysis

Figure 4:
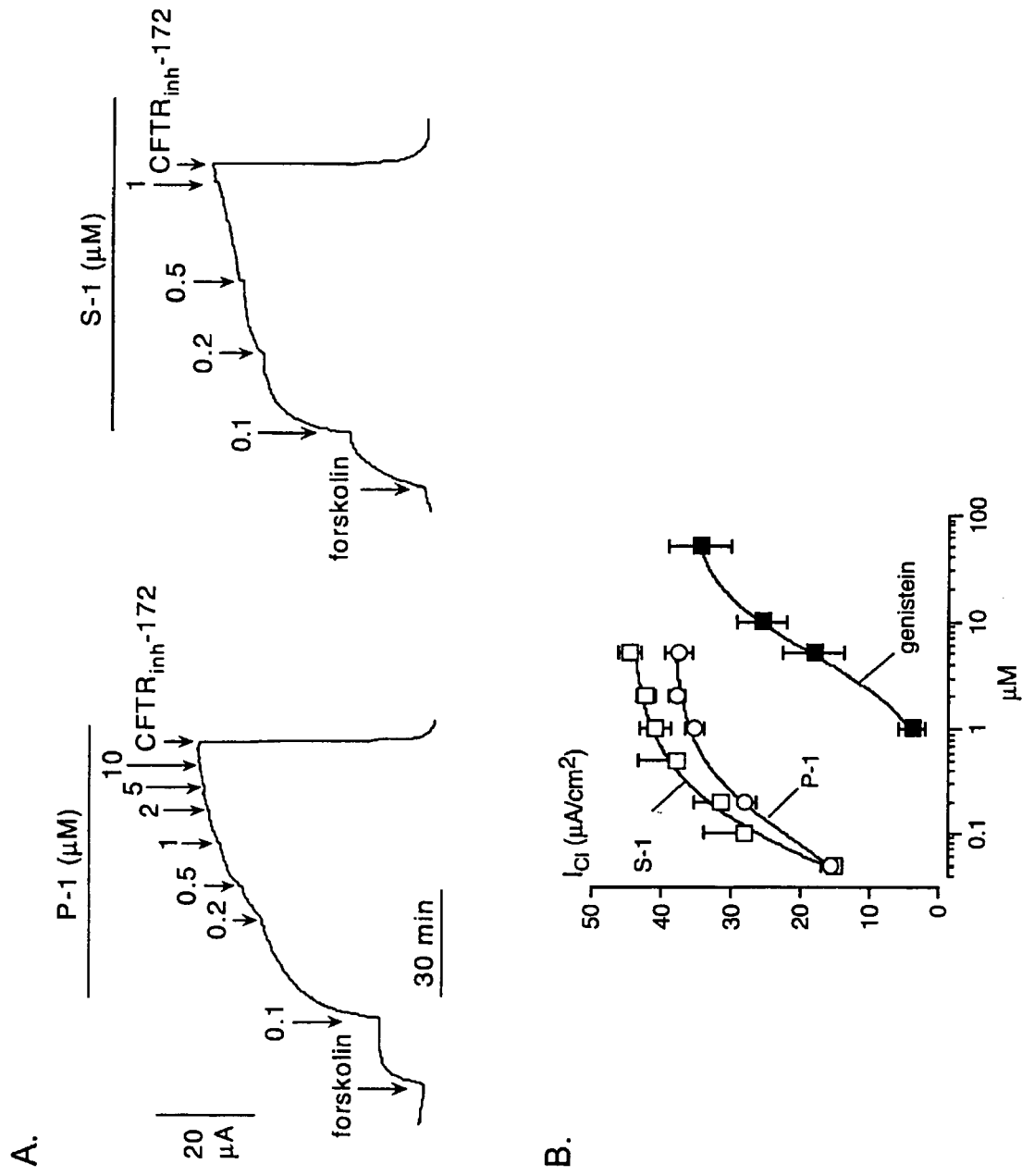
FIG. 4 provides graphs showing CFTR-mediated chloride currents measured in FRT cells expressing ΔF508-CFTR for the phenylglycine containing compound P-1 (Panel A, left), the sulfonamide containing compound S-1 (Panel A, right) in the presence of forskolin, and the average dose-responses for the compounds, with genistein data shown for comparison (SE, n=4) (Panel B).

Short-circuit current analysis was done on each of these compounds to confirm bona fide activation of ΔF508-CFTR Cl⁻ currents. Experiments were done after basolateral membrane permeabilization and in the presence of a transepithelial Cl⁻ gradient, so that short-circuit current represents apical membrane Cl⁻ current. Representative data are shown in FIG. 4, panel A. CFTR-mediated chloride currents measured in FRT cells expressing ΔF508-CFTR. Cells were plated on a permeable support to generate a polarized epithelium, cultured for 5-7 days, and then incubated at 27° C. for 24 hours. Transepithelial chloride current was measured in a modified Ussing chamber in the presence of a chloride gradient. Cells were maximally stimulated with forskolin (20 μM) and then with the indicated concentrations of the phenylglycine containing compound P-1 and the sulfonamide containing compound S-1. Specific activation of CFTR is demonstrated by the block of current caused by the thiazolidinone CFTR inhibitor CFTR$_{inh}$-172. The results show that the phenylglycine containing compound P-1 and the sulfonamide containing compound S-1 gave ΔF508-CFTR currents with potencies better than 100 nM, and maximal currents comparable to or greater than that produced by 50 μM genistein (see FIG. 3, panel B).

Figure 5:
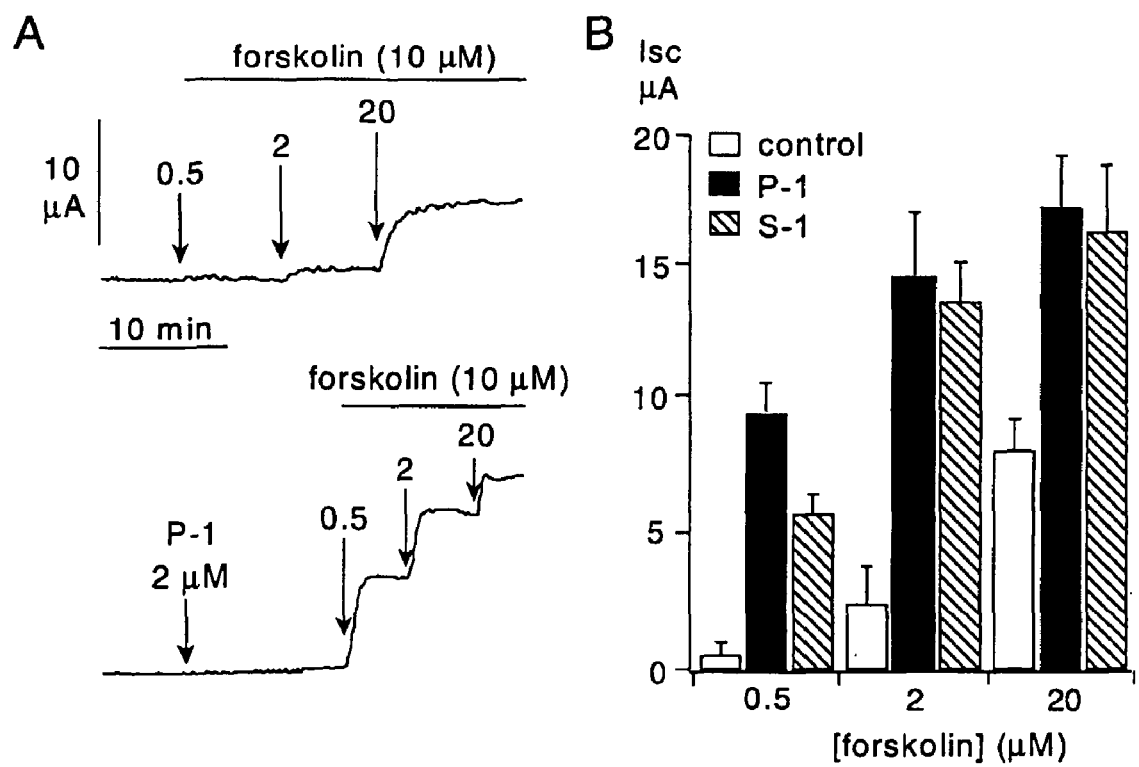
FIG. 5 provides the results of Ussing chamber experiments. Panel A provides representative traces showing potentiation of the response of ΔF508-CFTR to forskolin in the absence (upper graph) or presence (lower graph) of a phenylglycine containing compound (P-1). Panel B of FIG. 5 shows a summary of similar experiments for P-1 and a sulfonamide containing compound (S-1) which show significant increase in current induced by low concentrations of forskolin.

An interesting observation was that these new potentiators increased the sensitivity of ΔF508-CFTR to forskolin at low concentrations. FIG. 5 depicts the results with phenylglycine containing compounds and sulfonamide containing compounds showing potentiation of the response of ΔF508-CFTR to forskolin. FIG. 5, Panel A shows the representative traces obtained from Ussing chamber experiments show the effect of forskolin at increasing concentrations in the presence and the absence of the phenyglyicine containing compound P-1 (100 nM). FIG. 5, panel A shows that forskolin alone produces a small increase in current, with little effect at 2 μM and a larger effect at 20 μM (top). However, after preincubation with the phenylglycine potentiator, low concentrations of forskolin (0.5 μM) produce substantial currents (bottom). FIG. 5, Panel B shows a summary of similar experiments for the phenylglycine containing compound P-1 and the sulfonamide containing compound S-1 showing significant increase in current induced by low concentrations of forskolin.

Example 3 cAMP Analysis

Figure 6:
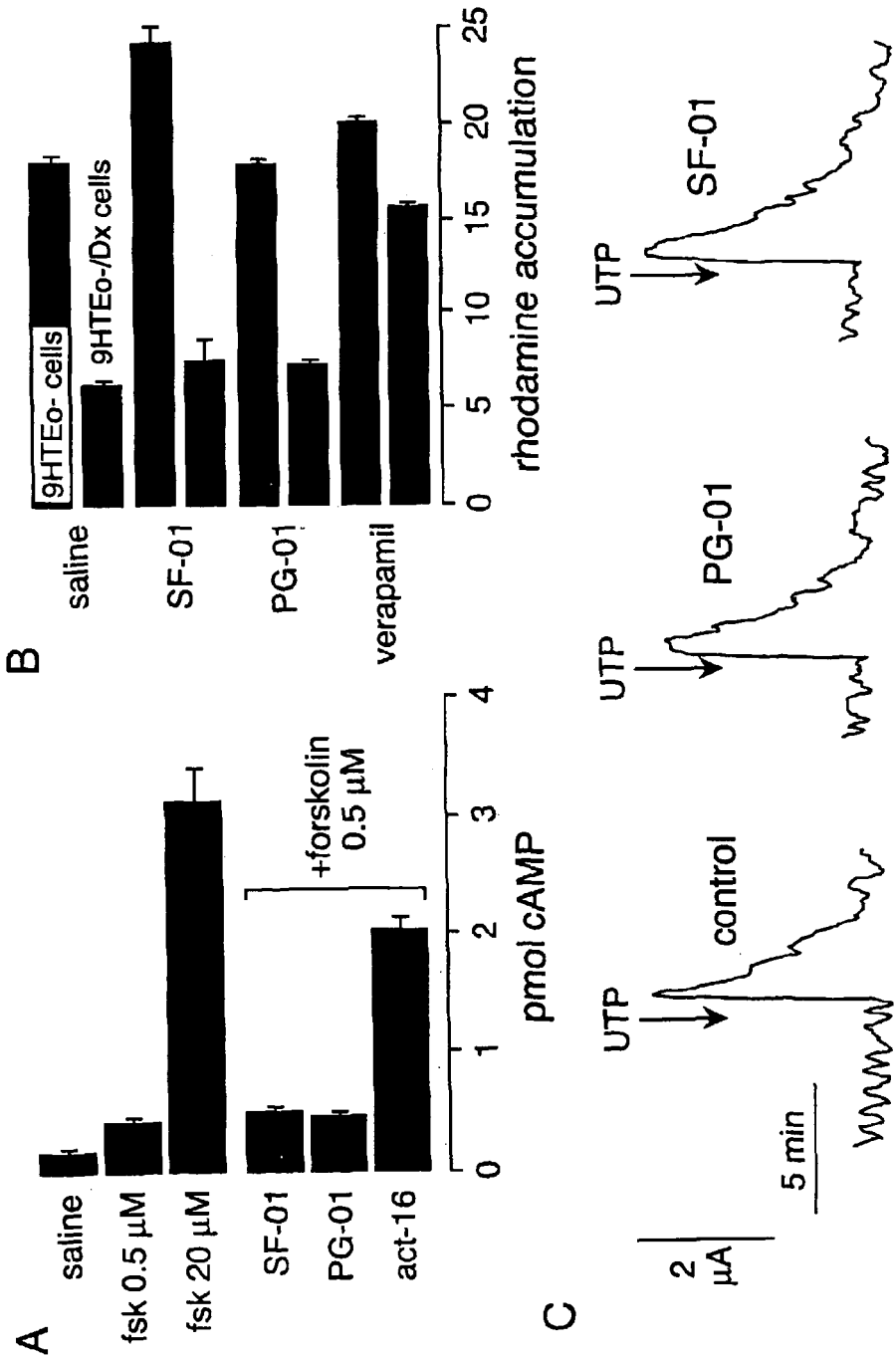
FIG. 6 shows the specificity of the subject compounds. Panel A shows intracellular cAMP concentration after forskolin addition with and without compounds P-1 and S-1 (2 μM). Panel B shows MDR-1 activity shown as rhodamine 123 accumulation in multidrug sensitive (9HTEo-) and multidrug resistant (9HTEo-/Dx) cells. Significant accumulation was found in 9HTEo-/Dx cells for verapamil (100 μM) but not for compounds P-1 and S-1 (5 μM). Panel C shows activation of Cl$^-$ current by apical UTP in polarized human bronchial epithelia. Pretreatment with ΔF508-CFTR activators (2 μM) did not affect the maximum current or time-course of the UTP response.

An analysis of compound specificity was also performed. Cells were incubated with potentiators in the presence of a low concentration of forskolin (0.5 μM), lysed, and assayed for cAMP. The results show that the compounds P-1 and S-1 did not increase cAMP above the level induced by forskolin 0.5 ZM alone (FIG. 6, panel A), whereas the compound CFTR$_{act}$-16, an indirect activator of CFTR (Ma et al., J. Biol. Chem. 277:37235-37241 (2002)), strongly increased cAMP. In addition, multiple drug resistance protein-1 (MDR-1) activity was assayed by intracellular accumulation of the fluorescent probe rhodamine 123. The wo cell lines used in the assay were the parental human tracheal cell line 9HTEo-, and its multidrug resistant subclone 9HTEo-/Dx that strongly expresses MDR-1 (Rasola et al., J. Biol. Chem. 269:1432-1436 (1994)). The results show that the 9HTEo-/Dx cells accumulate much less rhodamine 123 than 9HTEo-cells as a consequence of MDR-1 mediated dye extrusion. Dye accumulation was increased significantly by the MDR-1 inhibitor verapamil, but was not affected by compounds P-1 or S-1 (FIG. 6, panel B). In addition, effects on the UTP/calcium activated Cl$^-$ channel were measured from short circuit current measurements on human bronchial epithelial cells. The results show that compounds P-1 or S-1 had no effect on the magnitude or kinetics of the calcium-activated Cl$^-$ current (FIG. 6, panel C).

Based on the measurements of cellular cAMP concentrations, the results show that the apparent synergy of the compounds with forskolin is not due to cAMP elevation. The results show a direct interaction between the phenylglycine containing compounds and the sulfonamide containing compounds with ΔF508-CFTR. The lack of effect of the compounds in the absence of cAMP elevating agents and the apparent synergy with cAMP elevating agents are favorable properties in that near-relative CFTR regulation is recapitulated.

Example 4

Patch-Clamp Analysis

Patch-clamp analysis was done to establish the electrophysiological mechanism of ΔF508-CFTR activation. Representative single channel recordings shown in FIG. 7, panel A indicate strong activation of ΔF508-CFTR chloride channels at 100 nM concentrations of the phenylglycine and sulfonamide potentiators. Channel open probably (Po) was increased without change in channel unitary conductance. The subject compounds increased Po greatly over that by forskolin alone, to levels (~0.4) measured for wild-type CFTR measured under the same conditions.

Figure 7:
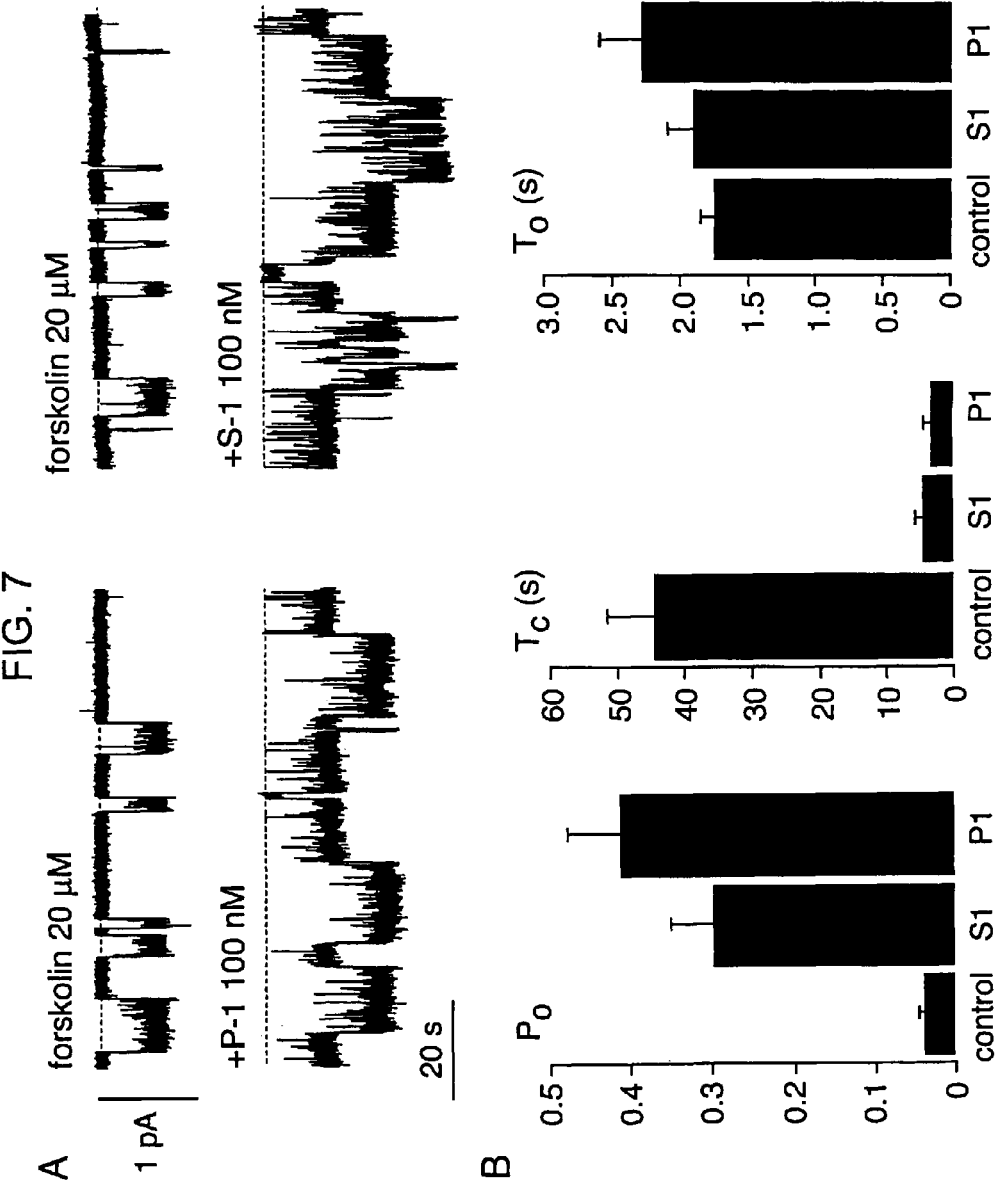
FIG. 7 provides graphs illustrating representative examples of potentiator effects as detected by patch-clamp analysis. Panel A shows cell-attached patch-clamp recordings of ΔF508-CFTR channel activity in the presence of forskolin (20 μM) (top portion) and after addition of the phenylglycine containing compound P-1 (100 nM) or the sulfonamide containing compound S-1 (bottom portion, 100 nm). Panel B is a series of graphs summarizing the average averaged channel open probabilities (Po) (left), mean closed time (T$_c$)(middle), and mean open time (T$_o$)(right) in the presence of forskolin alone or in combination with indicated compounds from the data of Panel A.

FIG. 7, panel A shows the results of the patch-clamp analysis. A. Cell-attached patch-clamp recordings show ΔF508-CFTR channel activity in the presence of forskolin (20 μM) (top) and after addition of the phenylglycine containing compound P-1 or sulfonamide containing compound S-1 (100 nM, bottom). The closed channel level is indicated by a dashed line. Downward deflections indicate channel opening. The large increase in channel activity caused by the potentiators seen by the appearance of multiple channel openings of long duration. FIG. 7, panel B shows the averaged channel open probabilities (P$_O$) (SEM) from data as in FIG. 7, panel A. In addition, analysis of gating kinetics shows that the increase in Po was due to a reduction in mean channel closed time (T$_c$) rather than an increase in mean channel open time (T$_O$) (FIG. 7, panel B).

Example 5

Native Human Airway Epithelial Cells

Figure 8:
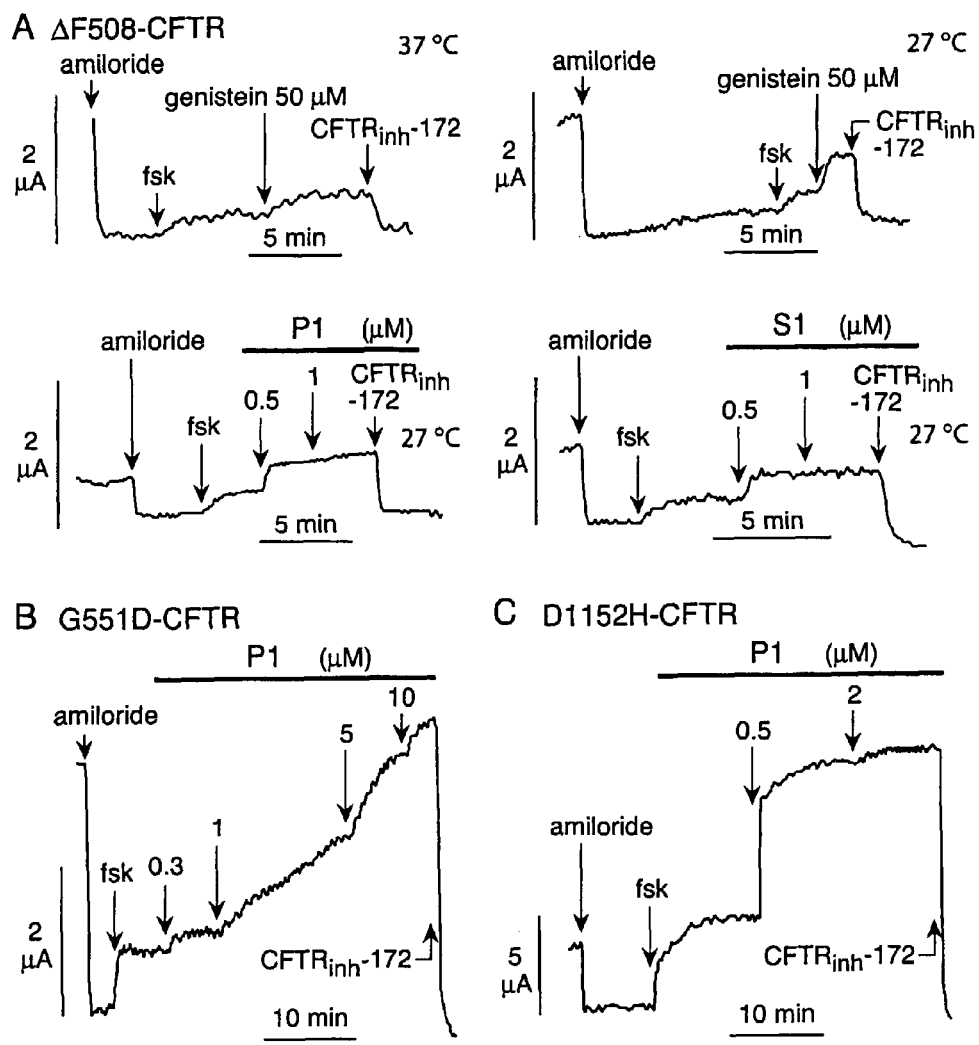
FIG. 8 is a set of graphs showing stimulation of Cl$^-$ secretion in CF human airway epithelial cells. Panel A shows ΔF508-CFTR activation in nasal epithelial cells from a ΔF508-CFTR homozygous subject after addition of compound P-1 (left panel, bottom portion), compound S-1 (right panel, bottom portion) in the presence of forskolin following addition of amiloride to block epithelial sodium channels, or genistein at either 37° C. (left panel, top portion) or 27° C. (right panel, top portion). Panel B shows G551D-CFTR activation in nasal epithelial cells from a G551D-CFTR homozygous subject after addition of compound P-1. Panel C shows D1152H-CFTR activation in nasal epithelial cells from a D1152H-CFTR homozygous subject after addition of compound P-1.

To demonstrate that the compounds identified by screening human ΔF508-CFTR in transfected epithelial cells also were effective in native human airway cells, short-circuit current measurements were done on primary cultures of nasal epithelial cells from a ΔF508 homozygous subject. Representative short-circuit data are shown in FIG. 8. Maximal ΔF508-CFTR activation was found for potentiator concentrations less than 500 nM, showing that the potentiators are effective in native human cells.

Human nasal epithelial cells from ΔF508 homozygote subjects were cultured as polarized monolayers on permeable supports for transepithelial short-circuit current measurement. After blocking the epithelial Na$^+$ channel with amiloride, forskolin (20 μM) was applied, followed by genistein, compound P-1, or compound S-1. CFTR$_{inh}$-172 was applied at the end of each study to determine total CFTR-dependent current. Cells maintained at 37° C. had little CFTR current, in agreement with the expected intracellular retention of ΔF508-CFTR. Low temperature rescue by incubation at 27° C. for 20-24 hours produced greater ΔF508-CFTR current, with significant activation by compounds P-1 and S-1 at nanomolar concentrations (FIG. 8, panel A). Stimulation by forskolin plus compound P-1 or compound S-1 was blocked by CFTR$_{inh}$-172. Genistein was comparably effective but at much higher concentrations.

In addition, primary cell cultures from subjects carrying CFTR mutations causing pure gating defects were also tested. For these studies cells were cultured at 37° C. The results show that nasal epithelial cells from a subject with the G551 D mutation (Zegarra-Moran et al., Br. J. Pharmacol. 137:504-512 (2002)) had a large response to compound P-1 after forskolin stimulation (FIG. 8, panel B). Cells from a subject having D1152H and ΔF508 CFTR mutations were also tested. The D1152H mutation affects the second nucleotide binding domain and causes a decrease in channel activity (Vankeerberghen et al., FEBS Lett. 437:1-4 (1998)). The results show that the D1152H/ΔF508 cells maintained at 37° C. cells had large CFTR currents in response to compound P-1 (FIG. 8, panel C).

Example 6

Correction of Defective Gating

To demonstrate that the phenylglycine containing compounds and sulfonamide containing compounds are also effective in activating other forms of mutant CFTR, the compounds were tested with the "class III" gating defective mutant CFTRs G551 D-CFTR and G1349D-CFTR. The G551D-CFTR and G1349D-CFTR mutations produce a severe gating defect without impairment in protein trafficking (Gregory et al., MCB 11:3886-3893 (1991). These mutations affect the glycine residues in NBD1 and NBD2 that are highly conserved in ATP-binding cassette proteins (Hyde et al., 1990; Logan et al., 1994). The G551D-CFTR gating defective mutant is the most common CFTR gating mutant that causes CF.

Figure 9:
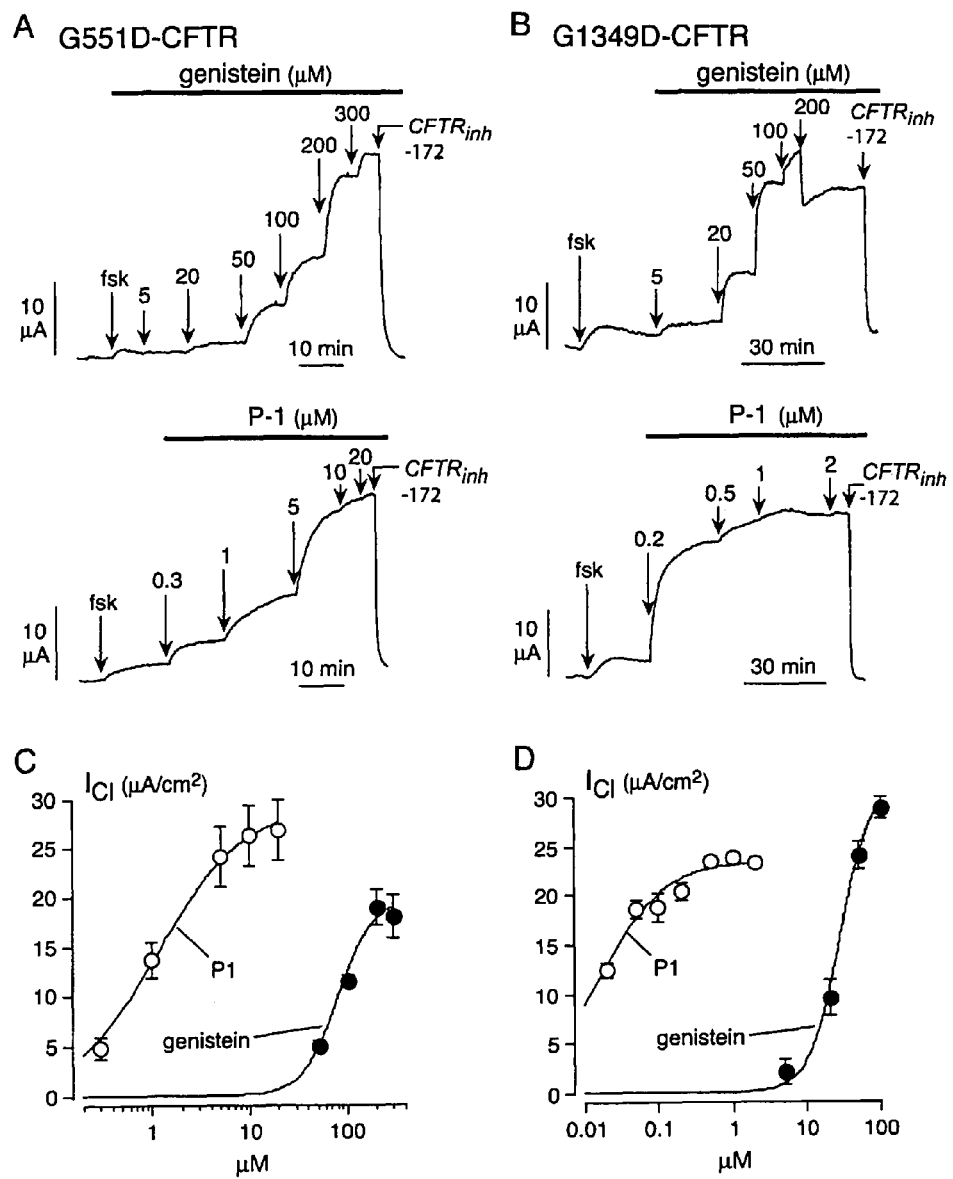
FIG. 9 shows results of activation of G551D- and G349D-CFTR mutants. Panels A and B show CFTR-mediated chloride currents measured in epithelial cells expressing either G551D-CFTR (Panel A) or G1349D-CFTR (Panel B) in response to the addition of either the phenylglycine containing compound P-1 (bottom portion of each panel) or genestein (top portion of each panel) in the presence of forskolin. Panels C and D are results of dose-response curves (SE, n=4) for compound P-1 and genistein for activation of G551 D-CFTR (Panel C) and G1349D-CFTR (Panel D).

Experiments were done after basolateral membrane permeabilization and in the presence of a transepithelial Cl⁻ gradient, so that short-circuit current represents apical membrane Cl⁻ current. Representative data are shown in FIG. 9, panel A. CFTR-mediated chloride currents measured in FRT cells expressing either G551D-CFTR (FIG. 9, panel A, left panel) or G1349D-CFTR (FIG. 9, panel A, right panel). Cells were plated on a permeable support to generate a polarized epithelium, cultured for 5-7 days, and then incubated at 27° C. for 24 hours. Transepithelial chloride current was measured in a modified Ussing chamber in the presence of a chloride gradient. Cells were maximally stimulated forskolin and then with the indicated concentrations of the phenylglycine containing compound P-1 (bottom portion of each panel) or genestein, a flavone compound known at high concentrations to correct gating defective mutant CFTRs (top portion of each panel). Specific activation of CFTR is demonstrated by the block of current caused by the thiazolidinone CFTR inhibitor $CFTR_{inh}$-172.

The G551D and G1349D mutant CFTRs produced little Cl⁻ current after addition of maximal forskolin (FIG. 9, panels A and B). Genistein, a known activator of G551D- and G1349D-CFTR, increased Cl⁻ current substantially, albeit at high micromolar concentrations (FIG. 9, panels A and B, top panels). Compound P-1 produced large currents in both G551D- and G1349D-CFTR expressing cells as shown in FIG. 9, panels A and B (bottom panels), and summarized in FIG. 9, panels C and D. The currents were sensitive to $CFTR_{inh}$-172 and not seen in non-transfected cells. The results show that the activating potency of P-1 was found to be 50-100 times better than that of genistein.

The results show that the phenylglycine containing compounds corrected defective gating in a number of CF-causing CFTR mutants including ΔF508, G551D, G1349D and D1152H. The G551D and G1349D mutations affect critical glycine residues in nucleotide binding domains 1 and 2 of CFTR, respectively (Hyde et al., Nature 346:362-365 (1990)), producing a pure gating defect of greater severity than that in ΔF508-CFTR (Gregory et. al., MCB 11:3886-3893 (1991); Logan et. al., J. Clin. Invest. 94:228-236 (1994); Zegarra-Moran et. al., Br. J. Pharmacol. 137:504-512 (2002); Derand et. al., JBC 277:35999-36004 (2002)). Forskolin alone produced little activation of these mutant CFTRs even at high concentrations, whereas compound P-1 after application of forskolin produced a >10-fold elevation in current. The results show that the $K_d$ for compound P-1 for G551D-CFTR activation was ~1 μM, approximately 100-fold better than that of genistein. The potency for activation of G1349D-CFTR by compound P-1 was even better, ~40 nM. In contrast to the ΔF508 mutation, other cystic fibrosis mutations, which number >1000, have a relatively very low frequency. The fraction of CF mutations that cause a pure gating defect (class III mutants) is unknown but is likely to be substantial. The results show that the phenylglycine containing compounds can be used in mono-drug therapy for many of these mutations.

Example 7

Correction of Defective Gating in Nasal Polyp Epithelial Cells

Figure 10:
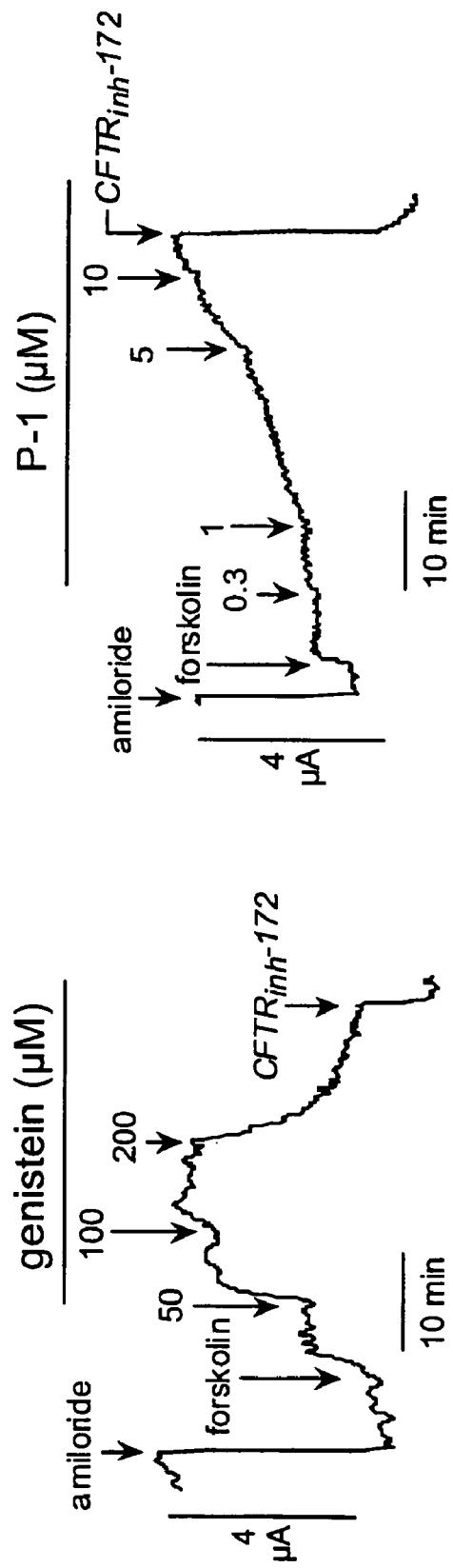
FIG. 10 is a set of graphs showing CFTR-mediated chloride currents measured in nasal polyp epithelial cells from a CF patient with G551D-CFTR mutation in response to the addition of either the phenylglycine containing compound P-1 (right panel) or genestein (left panel) in the presence of forskolin following addition of amiloride to block epithelial sodium channels.

To demonstrate that the phenylglycine containing compounds identified by screening human ΔF508-CFTR in transfected epithelial cells also were effective in correcting defective gating native human tissues, short-circuit current measurements were done on cultures of nasal polyp epithelial cells from a CF patient with the G551D-CFTR mutation. Representative short-circuit data are shown in FIG. 10. Maximal G551D-CFTR activation was found for potentiator concentrations less than 10 μM, indicating that the potentiators are effective in human nasal polyp epithelial cells.

FIG. 10 shows the results of the G551D-CFTR activity in nasal polyp epithelial cells from G551D-CFTR human subject in response to the subject compounds. Epithelial cells were plated on permeable supports to generate polarized monolayers resembling the epithelium in vivo. After blocking the epithelial sodium channel with amiloride, CFTR-dependent chloride secretion was stimulated with forskolin at maximal concentration. The phenylglycine containing compound P-1 further increased CFTR-mediated currents. This effect was fully blocked by CFTR inhibitor $CFTR_{inh}$-172.

Example 8

Hepatic Clearance of Compounds

Figure 11:
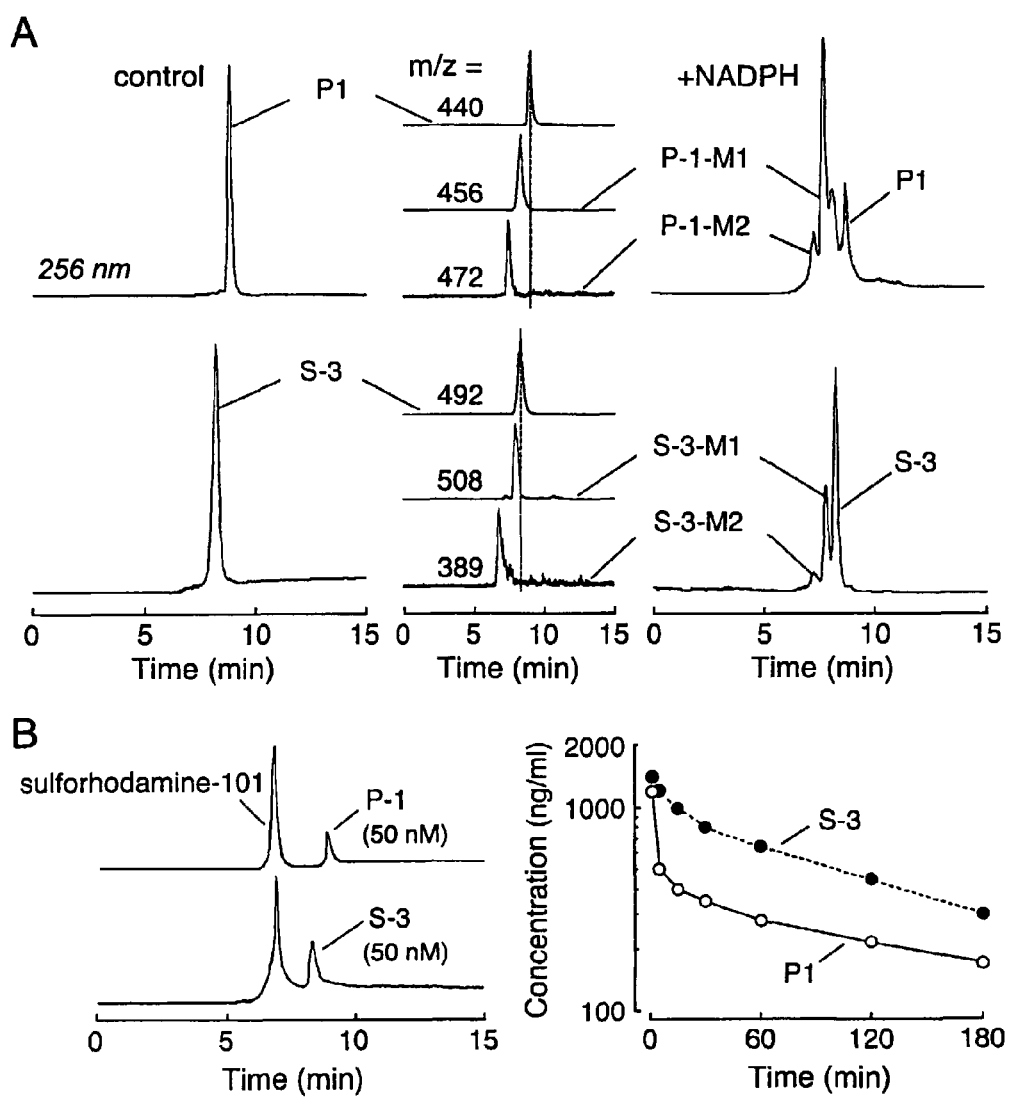
FIG. 11 shows liquid chromatography/mass spectrometry analysis of microsomal metabolites of compounds P-1 and S-3, and rat pharmacokinetics. Panel A shows results of the liquid chromatography/mass spectrometry analysis. Microsomes were incubated with compounds P-1 or S-3 (each 10 μM) in the absence (control) or presence of NADPH for 1 hour at 37° C. HPLC chromatograms at 256 nm for control (left) and NADPH (right) samples, and corresponding ion current chromatograms for positive ion electrospray mass spectrometry for indicated m/z (middle). M1, metabolite 1; M2, metabolite 2. Panel B shows pharmacokinetic analysis. The left panel shows the HPLC chromatogram of compounds P-1 and S-3 demonstrating assay sensitivity to better than 50 nM. The right panel shows the pharmacokinetics of compounds P-1 (open circles) and S-3 (closed circles) after 5 mg/Kg intravenous bolous injection (mean±SE, n=3-4 rats).

To predict hepatic clearance of compounds P-1 and S-3, in vitro incubations were done with rat hepatic microsomes for 1 hour at 37° C. in the absence (control) and presence of NADPH, followed by LCMS analysis. Compound S-3 was chosen for these studies as the most potent of the sulfonamide containing compounds. FIG. 11, panel A (top, left and right), shows representative HPLC chromatograms, with compound P-1 eluting at 7.85 min, and its two major metabolites (M1 and M2) eluting at 6.88 and 7.16 min. Mass spectrometry identified the original compound, and M1 and M2 with m/z 456 (~PG-01+OH; [M+1]⁺) and 472 (~P-1+2OH; [M+1]⁺), respectively (FIG. 11, panel A, top, middle). A minor metabolite was also detected at 7.43 min with m/z 428. Approximately 90% of compound P-1 was metabolized after incubation with microsomes for 1 hour in the presence of NADPH, and non-metabolized compound P-1 was not detectable after 2 hours. FIG. 11, panel A (bottom, left and right), shows the HPLC profile for compound S-3 and its two major metabolites eluting at 7.44 min and 7.16/6.77 min, respectively, with corresponding molecular ion peaks (FIG. 11, panel A, bottom, middle) at m/z 492 (S-3, [M+1]⁺), 508 (~S-3+OH, [M+1]⁺) and 389. Compound S-3 was ~35% degraded after a 1 hour incubation with liver microsomes in presence of NADPH.

Example 9

Pharmacokinetic Analysis of Compounds

Pharmacokinetic analysis of P-1 and S-3 in rats was done by serial measurements of plasma concentrations after single bolus infusions (5 mg/Kg). FIG. 11, panel B (left), shows HPLC chromatograms for compounds P-1 and S-3 (each at 50 nM added to control plasma and supplemented with sulforhodamine 101 as internal standard), demonstrating the sensitivity of the assay. Compound P-1 pharmacokinetics fitted a two-compartment model with half-times of approximately 0.2 hour and 1 hour, whereas compound S-3 clearance had elimination half-time of approximately 1.3 hours (FIG. 11, panel B, right).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A pharmaceutical composition comprising a compound of formula (I):

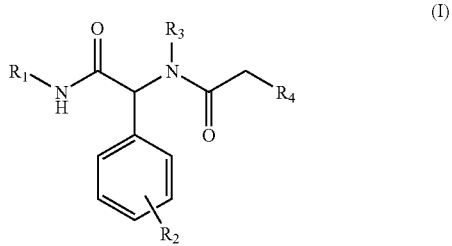

wherein $R_1$ is independently chosen from a substituted or unsubstituted phenyl group, a substituted or unsubstituted heteroaromatic group, or a cyclic or acyclic alkyl group; $R_2$ is independently chosen form a hydrogen, a alkyl group, an ether group, a halogen, or a perfluoroalkyl group; $R_3$ is independently chosen from a hydrogen or an alkyl group, and $R_4$ is independently chosen from a substituted or unsubstituted heteroaromatic group, or a alkanoyl-amine group; or a pharmaceutically acceptable derivative thereof, as an individual stereoisomer or a mixture thereof; or a pharmaceutically acceptable salt thereof.

2. The pharmaceutical composition of claim 1, wherein the composition further comprises at least one of a pharmaceutically acceptable carrier, a pharmaceutically acceptable diluent, a pharmaceutically acceptable excipient and a pharmaceutically acceptable adjuvant.

3. The pharmaceutical composition of claim 1, wherein the composition does not contain detectable dimethyl sulfoxide.

4. The pharmaceutical composition of claim 1, wherein the compound is chosen from: 2-[(2-1H-Indol-3-yl-acetyl)-methyl-amino]-N-(4-isopropyl-phenyl)-2-phenyl-acetamide; 2-[(2-1H-Indol-3-yl-acetyl)-methyl-amino]-N-(4-isopropyl-phenyl)-2-(4-methoxy-phenyl)-acetamide; 2-[(2-1H-Indol-3-yl-acetyl)-methyl-amino]-N-(4-methoxy-phenyl)-2-phenyl-acetamide; 2-[(2-1H-Indol-3-yl-acetyl)-methyl-amino]-2,N-bis-(4-methoxy-phenyl)-acetamide; N-(2,3-Dihydro-benzo[1,4]dioxin-6-yl)-2-(2-1H-indol-2-yl-acetylamino)-2-p-tolyl-acetamide; N-(2,3-Dihydro-benzo[1,4]dioxin-6-yl)-2-[(2-1H-indol-3-yl-acetyl)-methyl-amino]-2-(4-methoxy-phenyl)-acetamide; 2-(2-1H-Indol-3-yl-acetylamino)-N-(4-isopropyl-phenyl)-2-phenyl-acetamide; N-Benzo[1,3]dioxol-5-yl-2-[(2-1H-indol-3-yl-acetyl)-methyl-amino]-2-p-tolyl-acetamide; or 2-[(2-Acetylamino-acetyl)-methyl-amino]-N-(2,3-dihydro-benzo[1,4]dioxin-6-yl)-2-phenyl-acetamide.

5. The pharmaceutical composition of claim 1, wherein $R_1$ is chosen from a phenyl group substituted by a hydrogen, a methyl group, an isobutanyl group, or a methoxyl group.

6. The pharmaceutical composition of claim 1, wherein $R_2$ is chosen from a hydrogen, a methyl group, or a methoxyl group.

7. The pharmaceutical composition of claim 1, wherein $R_3$ is chosen from a hydrogen or a methyl group.

8. The pharmaceutical composition of claim 1, wherein $R_4$ is chosen from an indole group or an alkanoylamino group.

9. The pharmaceutical composition of claim 1, wherein $R_1$ is independently chosen from a substituted or unsubstituted heteroaromatic group; $R_2$ is independently chosen form a hydrogen, a alkyl group, or an ether group; $R_3$ is independently chosen from a hydrogen or an alkyl group, and $R_4$ is independently chosen from a substituted or unsubstituted heteroaromatic group, or a alkanoylamino group.

10. The pharmaceutical composition of claim 9, wherein $R_1$ is a 2,3-dihydro-benzo[1,4]dioxine group.

11. The pharmaceutical composition of claim 9, wherein $R_2$ is chosen from a hydrogen, a methyl group, or a methoxyl group.

12. The pharmaceutical composition of claim 9, wherein $R_3$ is chosen from a hydrogen or a methyl group.

13. The pharmaceutical composition of claim 9, wherein $R_4$ is chosen from an indole group or an isopropenylamine group.

14. A pharmaceutical composition of claim 1, comprising a compound of formula:

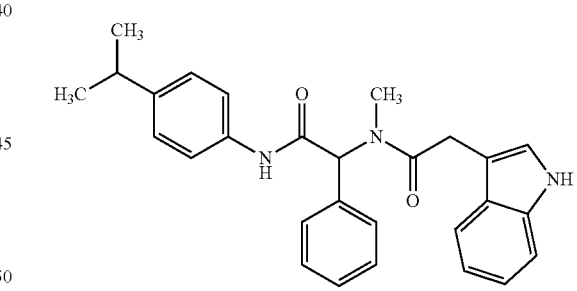

or a stereoisomer or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,939,558 B2 | Page 1 of 1 |
| APPLICATION NO. | : 11/628411 | |
| DATED | : May 10, 2011 | |
| INVENTOR(S) | : Alan S. Verkman | |

It is certified that error appears in the above-identified patent and that said Letters Patent is hereby corrected as shown below:

Column 1, lines 8-11 insert the following paragraph:

--This invention was made with government support under federal grant nos. HL73856, EB00415, HL59198, EY13574, and DK35124 awarded by the National Institutes of Health. The United States Government has certain rights in this invention.--

Signed and Sealed this
Tenth Day of January, 2012

David J. Kappos
*Director of the United States Patent and Trademark Office*